US012733871B2

(12) United States Patent
Omiya et al.

(10) Patent No.: US 12,733,871 B2
(45) Date of Patent: Sep. 15, 2026

(54) INFORMATION PROCESSING DEVICE, INFORMATION PROCESSING METHOD, INFORMATION PROCESSING SYSTEM AND INFORMATION PROCESSING PROGRAM

(71) Applicant: PST INC., Kanagawa (JP)

(72) Inventors: Yasuhiro Omiya, Kanagawa (JP); Masaru Suzuki, Kanagawa (JP)

(73) Assignee: PST INC., Kanagawa (JP)

( * ) Notice: Subject to any disclaimer, the term of this patent is extended or adjusted under 35 U.S.C. 154(b) by 742 days.

(21) Appl. No.: 18/001,118

(22) PCT Filed: Jun. 11, 2020

(86) PCT No.: PCT/JP2020/023049

§ 371 (c)(1),
(2) Date: Dec. 8, 2022

(87) PCT Pub. No.: WO2021/250854

PCT Pub. Date: Dec. 16, 2021

(65) Prior Publication Data

US 2023/0210451 A1 Jul. 6, 2023

(51) Int. Cl.
*A61B 5/00* (2006.01)

(52) U.S. Cl.
CPC .......... *A61B 5/4803* (2013.01); *A61B 5/4088* (2013.01)

(58) Field of Classification Search
CPC ..... A61B 5/165; A61B 5/4076; A61B 5/4088; A61B 5/4803; A61B 5/7264; G16H 20/70; G16H 50/20; G16H 50/30; G16H 50/70
See application file for complete search history.

(56) References Cited

U.S. PATENT DOCUMENTS 9,739,783 B1 8/2017 Kumar et al.
2017/0252922 A1 9/2017 Levine et al.
(Continued)

FOREIGN PATENT DOCUMENTS

CN 110495854 A 11/2019
JP 2019187492 A 10/2019

OTHER PUBLICATIONS

Chlasta, Karol, Krzysztof Wołk, and Izabela Krejtz. "Automated speech-based screening of depression using deep convolutional neural networks." Procedia Computer Science 164 (2019): 618-628. (Year: 2019).*

(Continued)

*Primary Examiner* — Benjamin S Melhus
(74) *Attorney, Agent, or Firm* — Hoffman Warnick LLC

(57) ABSTRACT

An information processing apparatus extracts a feature value which is an acoustic parameter from audio data. The information processing apparatus generates a spectrogram image of the audio data. The information processing apparatus calculates, on the basis of the feature value and a calculation model, a first score which indicates the extent of a user's psychiatrically-based disorder or neurologically-based disorder, or mental disorder symptom or cognitive dysfunction symptom. The information processing apparatus inputs the spectrogram image to a learned model, and calculates a second score which indicates the extent of the user's psychiatrically-based disorder or neurologically-based disorder, or mental disorder symptom or cognitive dysfunction symptom. The information processing apparatus combines the first score and the second score to calculate a combined score which indicates the extent of the user's psychiatrically-based disorder or neurologically-based disorder, or mental disorder symptom or cognitive dysfunction symptom. The information processing apparatus estimates (Continued)

whether the user has any of the disorders or symptoms according to the combined score.

10 Claims, 22 Drawing Sheets

(56) References Cited

U.S. PATENT DOCUMENTS

| | | | |
|---|---|---|---|
| 2020/0012922 | A1 | 1/2020 | Tanabe et al. |
| 2020/0118458 | A1 | 4/2020 | Shriberg et al. |
| 2020/0143526 | A1 | 5/2020 | Wang et al. |
| 2021/0121125 | A1 | 4/2021 | Tokuno et al. |

OTHER PUBLICATIONS

Z. Wang, L. Chen, L. Wang and G. Diao, "Recognition of Audio Depression Based on Convolutional Neural Network and Generative Antagonism Network Model," in IEEE Access, vol. 8, pp. 101181-101191, 2020, doi: 10.1109/ACCESS.2020.2998532. (Year: 2020).*

PCT International Search Report for International Application No. PCT/JP2020/023049, dated Aug. 11, 2020, 2 pages.

He et al., "Deep Residual Learning for Image Recognition,", In Proc. of CVPR, 2016, 9 pages.

He, Lang et al., "Automated depression analysis using convolutional neural networks from speech," Journal of Biomedical Informatics, 2018, vol. 83, pp. 103-111.

Extended European Search Report for Application 20940116.5, dated Feb. 6, 2024, 10 pages.

Emna Rejaibi et al., "Towards Robust Deep Neural Networks for Affect and Depression Recognition", arxiv.org, Cornell University Library, Nov. 2019, 8 pages.

Emna Rejaibi et al., "Clinical Depression and Affect Recognition with EmoAudioNet," arxiv.org, Cornell University Library, Nov. 2019, 11 pages.

Srimadhur et al., "An End-to-End Model for Detection and Assessment of Depression Levels using Speech," Procedia Computer Science, Elsevier, vol. 171, Jan. 2020, 10 pages.

* cited by examiner

FIG.6

| ID | SPECTROGRAM IMAGE | CORRECT ANSWER LABEL |
|---|---|---|
| 00001 | A1 | B1 |
| 00002 | A2 | B2 |
| ... | ... | ... |
| N | AN | BN |

| ID | FEATURE AMOUNT GROUP | CORRECT ANSWER LABEL |
|---|---|---|
| 00001 | C1 | D1 |
| 00002 | C2 | D2 |
| ... | ... | ... |
| M | CM | DM |

310
18
MICRO PHONE
12
TERMINAL COMMUNICATION SECTION
313
DISPLAY PORTION
315
19
314
ACQUIRING SECTION
20
EXTRACTING SECTION
22
GENERATING SECTION
24
FIRST SCORE CALCULATING SECTION
30
SECOND SCORE CALCULATING SECTION
32
COMPOSITE SCORE CALCULATING SECTION
34
INFERRING SECTION
36
COMMUNICATION SECTION
38
CALCULATION MODEL STORAGE
26
LEARNED MODEL STORAGE
28

410
414
ACQUIRING SECTION
20
GENERATING SECTION
24
EXTRACTING SECTION
42
SCORE CALCULATING SECTION
44
INFERRING SECTION
46
CALCULATION MODEL STORAGE
26
LEARNED MODEL STORAGE
28
MICRO PHONE
12
DISPLAY DEVICE
16

FIG.17

| Phrase | | Ph. 01 | Ph. 02 | Ph. 05 | Ph. 11 | Ph. 12 | Ph. 13 | Ph. 14 | Ph. 15 | Ph. 16 | Ph. 17 | Ph. 18 | Ph. 19 | Ph. 20 | Ph. 21 | Ph. 22 | Ph. 23 | Ph. 24 |
|---|---|---|---|---|---|---|---|---|---|---|---|---|---|---|---|---|---|---|
| INFERENCE FROM SECOND SCORE | others | 0.948 | 0.955 | 0.968 | 0.961 | 0.961 | 0.949 | 0.942 | 0.961 | 0.974 | 0.968 | 0.89 | 0.91 | 0.871 | 0.935 | 0.948 | 0.961 | 0.968 |
| | CI | 0.792 | 0.816 | 0.824 | 0.792 | 0.784 | 0.824 | 0.824 | 0.864 | 0.832 | 0.8 | 0.704 | 0.536 | 0.792 | 0.824 | 0.824 | 0.76 | 0.784 |
| INFERENCE FROM FIRST SCORE | others | 0.8 | 0.871 | 0.761 | 0.832 | 0.755 | 0.735 | 0.91 | 0.813 | 0.858 | 0.91 | 0.8 | 0.871 | 0.903 | 0.761 | 0.8 | 0.819 | 0.832 |
| | CI | 0.585 | 0.528 | 0.628 | 0.447 | 0.634 | 0.545 | 0.407 | 0.52 | 0.602 | 0.407 | 0.628 | 0.553 | 0.642 | 0.659 | 0.537 | 0.407 | 0.455 |
| INFERENCE FROM COMPOSITE SCORE | others | 0.942 | 0.955 | 0.968 | 0.961 | 0.955 | 0.961 | 0.955 | 0.955 | 0.974 | 0.968 | 0.89 | 0.929 | 0.89 | 0.955 | 0.948 | 0.968 | 0.968 |
| | CI | 0.768 | 0.816 | 0.824 | 0.8 | 0.808 | 0.8 | 0.8 | 0.864 | 0.832 | 0.784 | 0.712 | 0.544 | 0.808 | 0.8 | 0.792 | 0.752 | 0.744 |

FIG.19

| | | RESULTS OF INFERENCE | | | |
|---|---|---|---|---|---|
| | | CTRL | CI | MDs | (%) |
| CORRECT ANSWER LABEL | CTRL | 17 | 6 | 5 | 60.7 |
| | CI | 16 | 108 | 0 | 87.1 |
| | MDs | 27 | 5 | 95 | 74.8 |

FIG.20

| | | RESULTS OF INFERENCE | | | |
|---|---|---|---|---|---|
| | | CTRL | CI | MDs | (%) |
| CORRECT ANSWER LABEL | CTRL | 17 | 6 | 5 | 60.7 |
| | CI | 15 | 109 | 0 | 87.9 |
| | MDs | 26 | 5 | 96 | 75.6 |

FIG.21

| | | RESULTS OF INFERENCE | | | |
|---|---|---|---|---|---|
| | | CTRL | CI | MDs | (%) |
| CORRECT ANSWER LABEL | CTRL | 17 | 7 | 4 | 60.7 |
| | CI | 14 | 110 | 0 | 88.7 |
| | MDs | 22 | 5 | 100 | 78.7 |

FIG.22

| | | RESULTS OF INFERENCE | | | |
|---|---|---|---|---|---|
| | | CTRL | CI | MDs | (%) |
| CORRECT ANSWER LABEL | CTRL | 18 | 5 | 5 | 64.3 |
| | CI | 15 | 109 | 0 | 87.9 |
| | MDs | 23 | 5 | 99 | 78.0 |

INFORMATION PROCESSING DEVICE, INFORMATION PROCESSING METHOD, INFORMATION PROCESSING SYSTEM AND INFORMATION PROCESSING PROGRAM

TECHNICAL FIELD

The technique of the disclosure relates to an information processing device, an information processing method, an information processing system and an information processing program.

BACKGROUND ART

International Patent Application Publication No. 2020/013296 discloses a device that infers a psychological disorder or a neurological disorder. This device calculates various acoustic parameters from voice data of a user, and, by using these acoustic parameters, infers whether or not the user has a psychological disorder or a neurological disorder.

SUMMARY OF INVENTION

Technical Problem

The device disclosed in aforementioned International Patent Application Publication No. 2020/013296 infers a disorder by using acoustic parameters calculated from voice data, but there is room for improvement in the accuracy thereof.

The technique of the present disclosure was made in view of the above-described circumstances, and provides an information processing device, an information processing method, an information processing system and an information processing program that can accurately infer whether or not a user has a psychological disorder or a neurological disorder, or a symptom of a psychological disturbance or a symptom of a cognitive impairment, as compared with a case in which a psychological disorder or a neurological disorder, or a psychological disturbance symptom or a cognitive impairment symptom, is inferred by using parameters extracted from time series data of a voice uttered by a user.

Solution to Problem

In order to achieve the above-described object, a first aspect of the present disclosure is an information processing device comprising: an acquisition section configured to acquire voice data that is time series data of a voice uttered by a user; an extraction section configured to extract a feature amount, which is a predetermined acoustic parameter, from the voice data acquired by the acquisition section; a generation section configured to generate a spectrogram image expressing a spectrogram of the voice data, by carrying out frequency analysis on the voice data acquired by the acquisition section; a first score calculation section configured to calculate a first score, which expresses an extent to which the user has a psychological disorder or a neurological disorder, or a psychological disturbance symptom or a cognitive impairment symptom, on the basis of the feature amount extracted by the extraction section and a calculation model that is set in advance and is for calculating, from the feature amount, a score expressing an extent of a psychological disorder or a neurological disorder, or a psychological disturbance symptom or a cognitive impairment symptom; a second score calculation section configured to input the spectrogram image generated by the generation section into a learned model, which has been learned in advance and is for calculating, from the spectrogram image, a score expressing an extent of a psychological disorder or a neurological disorder, or a psychological disturbance symptom or a cognitive impairment symptom, and to calculate a second score expressing an extent to which the user has a psychological disorder or a neurological disorder, or a psychological disturbance symptom or a cognitive impairment symptom; a composite score calculation section configured to calculate, by combining the first score and the second score, a composite score expressing an extent to which the user has a psychological disorder or a neurological disorder, or a psychological disturbance symptom or a cognitive impairment symptom; and an inference section configured to infer whether or not the user has any disorder or symptom, in accordance with the composite score calculated by the composite score calculation section.

A second aspect of the present disclosure is an information processing device comprising: an acquisition section configured to acquire voice data that is time series data of a voice uttered by a user; a generation section configured to generate a spectrogram image expressing a spectrogram of the voice data, by carrying out frequency analysis on the voice data acquired by the acquisition section; an extraction section configured to extract a feature amount, which is a predetermined acoustic parameter, from the voice data acquired by the acquisition section, and, by using a learned model, to extract a feature amount from the spectrogram image generated by the generation section; a score calculation section configured to calculate a first score, which expresses an extent to which the user has a psychological disorder or a neurological disorder, or a psychological disturbance symptom or a cognitive impairment symptom, on the basis of the feature amounts extracted by the extraction section and a calculation model that is set in advance and is for calculating, from the feature amounts, a score expressing an extent of a psychological disorder or a neurological disorder, or a psychological disturbance symptom or a cognitive impairment symptom; and an inference section configured to infer whether or not the user has any disorder or symptom, in accordance with the score calculated by the score calculation section, wherein the learned model is a learned model that has been learned in advance by teacher data in which a spectrogram image for learning, and a correct answer label expressing a disorder or symptom of a user who uttered the voice data corresponding to the spectrogram image for learning, are associated with one another.

A third aspect of the present disclosure is an information processing device comprising: an acquisition section configured to acquire voice data that is time series data of a voice uttered by a user; an extraction section configured to extract a feature amount, which is a predetermined acoustic parameter, from the voice data acquired by the acquisition section; a generation section configured to generate an image corresponding to the voice data acquired by the acquisition section; a first score calculation section configured to input the feature amount extracted by the extraction section into a first learned model that has been learned in advance and is for calculating, from the feature amount, a score expressing an extent of a psychological disorder or a neurological disorder, or a psychological disturbance symptom or a cognitive impairment symptom, and to calculate a first score expressing an extent to which the user has a psychological disorder or a neurological disorder, or a psychological disturbance symptom or a cognitive impairment symptom; a second score calculation section configured to input the image generated by the generation section into a second learned model that has been learned in advance and is for calculating, from the image, a score expressing an extent of a psychological disorder or a neurological disorder, or a psychological disturbance symptom or a cognitive impairment symptom, and to calculate a second score expressing an extent to which the user has a psychological disorder or a neurological disorder, or a psychological disturbance symptom or a cognitive impairment symptom; a composite score calculation section configured to calculate, by combining the first score and the second score, a composite score expressing an extent to which the user has a psychological disorder or a neurological disorder, or a psychological disturbance symptom or a cognitive impairment symptom; and an inference section configured to infer whether or not the user has any disorder or symptom, in accordance with the composite score calculated by the composite score calculation section.

A fourth aspect of the present disclosure is an information processing method, according to which a computer executes processing comprising: acquiring voice data that is time series data of a voice uttered by a user; extracting a feature amount, which is a predetermined acoustic parameter, from the voice data; generating a spectrogram image expressing a spectrogram of the voice data, by carrying out frequency analysis on the voice data; calculating a first score, which expresses an extent to which the user has a psychological disorder or a neurological disorder, or a psychological disturbance symptom or a cognitive impairment symptom, on the basis of the feature amount and a calculation model that is set in advance and is for calculating, from the feature amount, a score expressing an extent of a psychological disorder or a neurological disorder, or a psychological disturbance symptom or a cognitive impairment symptom; inputting the spectrogram image into a learned model, which has been learned in advance and is for calculating, from the spectrogram image, a score expressing an extent of a psychological disorder or a neurological disorder, or a psychological disturbance symptom or a cognitive impairment symptom, and calculating a second score expressing an extent to which the user has a psychological disorder or a neurological disorder, or a psychological disturbance symptom or a cognitive impairment symptom; calculating a composite score expressing an extent to which the user has a psychological disorder or a neurological disorder, or a psychological disturbance symptom or a cognitive impairment symptom, by combining the first score and the second score; and inferring whether or not the user has any disorder or symptom, in accordance with the composite score.

A fifth aspect of the present disclosure is an information processing program executable by a computer to perform processing comprising: acquiring voice data that is time series data of a voice uttered by a user; extracting a feature amount, which is a predetermined acoustic parameter, from the voice data; generating a spectrogram image expressing a spectrogram of the voice data, by carrying out frequency analysis on the voice data; calculating a first score, which expresses an extent to which the user has a psychological disorder or a neurological disorder, or a psychological disturbance symptom or a cognitive impairment symptom, on the basis of the feature amount and a calculation model that is set in advance and is for calculating, from the feature amount, a score expressing an extent of a psychological disorder or a neurological disorder, or a psychological disturbance symptom or a cognitive impairment symptom; inputting the spectrogram image into a learned model, which has been learned in advance and is for calculating, from the spectrogram image, a score expressing an extent of a psychological disorder or a neurological disorder, or a psychological disturbance symptom or a cognitive impairment symptom, and calculating a second score expressing an extent to which the user has a psychological disorder or a neurological disorder, or a psychological disturbance symptom or a cognitive impairment symptom; calculating a composite score expressing an extent to which the user has a psychological disorder or a neurological disorder, or a psychological disturbance symptom or a cognitive impairment symptom, by combining the first score and the second score; and inferring whether or not the user has any disorder or symptom, in accordance with the composite score.

Advantageous Effects of Invention

In accordance with the technique of the disclosure, there is the effect that it can be accurately inferred whether or not a user has a psychological disorder or a neurological disorder, or a symptom of a psychological disturbance or a symptom of a cognitive impairment, as compared with a case in which a psychological disorder or a neurological disorder, or a psychological disturbance symptom or a cognitive impairment symptom, is inferred by using parameters extracted from time series data of a voice uttered by a user.

BRIEF DESCRIPTION OF DRAWINGS

FIG. 6 is a drawing for explaining teacher data.

FIG. 8 is a drawing illustrating an example of processings executed by the information processing device of the first embodiment.

FIG. 10 is a drawing for explaining teacher data.

FIG. 17 is a drawing illustrating effects of Example 1.
FIG. 19 is a drawing illustrating effects of Example 2.
FIG. 20 is a drawing illustrating effects of Example 2.
FIG. 21 is a drawing illustrating effects of Example 2.
FIG. 22 is a drawing illustrating effects of Example 2.

DESCRIPTION OF EMBODIMENTS

Embodiments of the technique of the disclosure are described in detail hereinafter with reference to the drawings.

<Information Processing System of First Embodiment>

Figure 1:
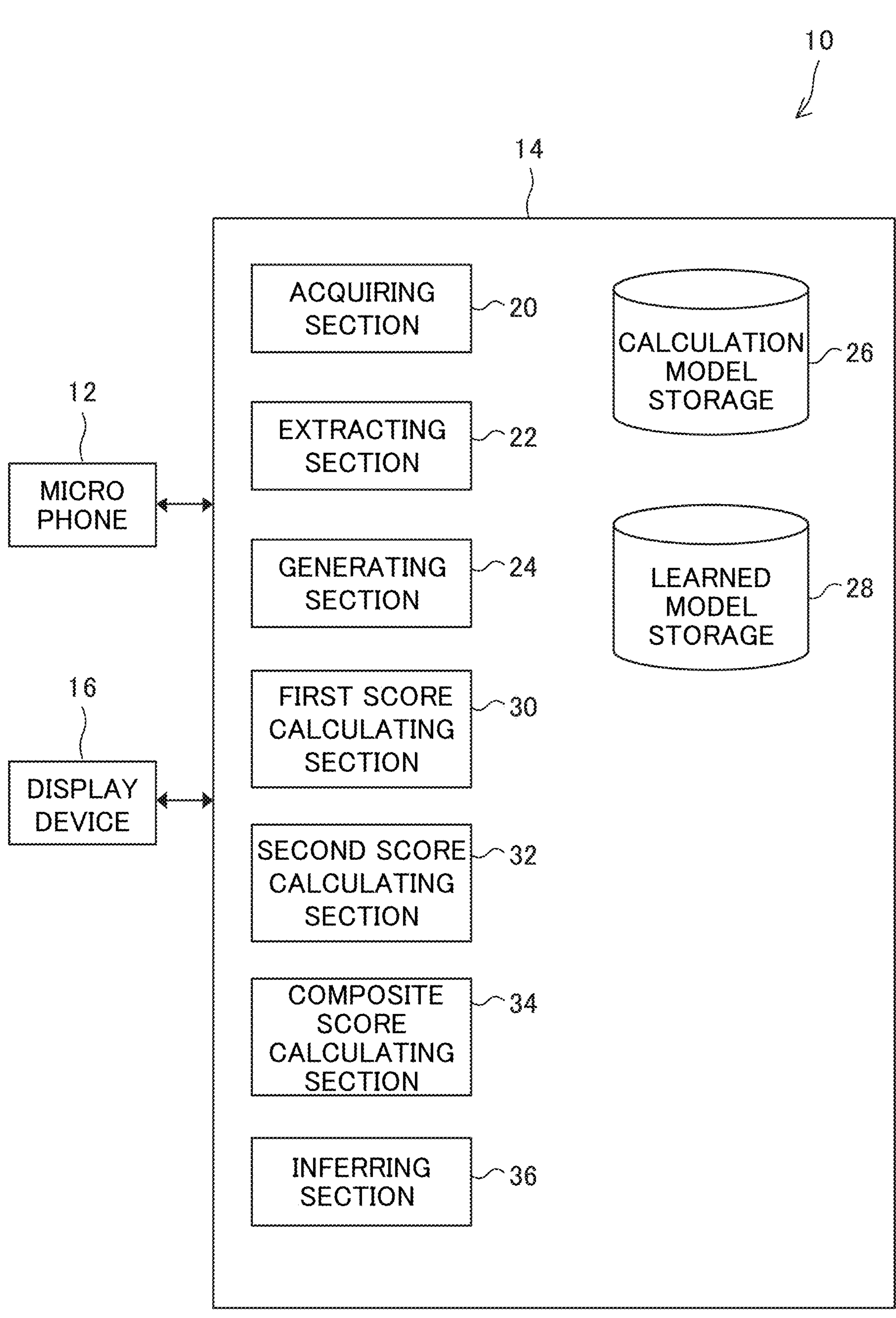
FIG. 1 is a drawing illustrating an example of the schematic structure of an information processing system of a first embodiment.

An information processing system 10 relating to a first embodiment is illustrated in FIG. 1. As illustrated in FIG. 1, the information processing system 10 of the first embodiment has a microphone 12, an information processing device 14 and a display device 16.

On the basis of the voice of a user that is picked-up by the microphone 12, the information processing system 10 infers whether or not the user has a psychological disorder or a neurological disorder, or a symptom of a psychological disturbance or a symptom of a cognitive impairment (which are also simply called "a psychological disorder, a neurological disorder or a symptom of these" hereinafter).

Figure 2:
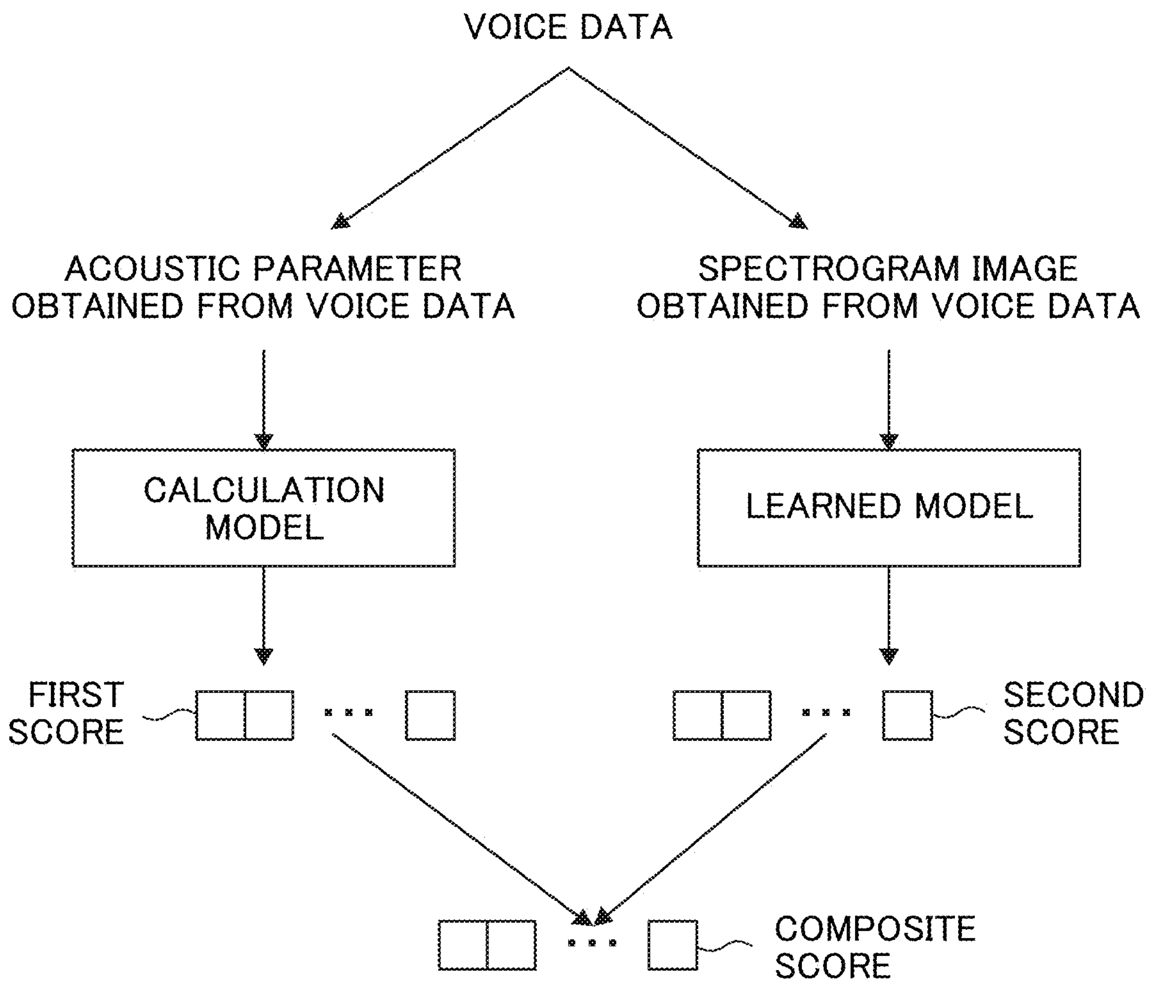
FIG. 2 is a drawing for explaining an overview of the first embodiment.

FIG. 2 is a drawing for explaining an overview of the information processing system 10 of the first embodiment. The information processing device 14 of the information processing system 10 of the first embodiment extracts acoustic parameters from voice data that is time series data of the voice uttered by the user. Further, the information processing device 14 generates a spectrogram image by carrying out frequency analysis on the voice data of the user.

Next, as illustrated in FIG. 2, the information processing device 14 inputs the acoustic parameters to a calculation model that is for calculating, from the acoustic parameters, first scores expressing the extents of having psychological disorders, neurological disorders or symptoms of these. Then, as illustrated in FIG. 2, the information processing device 14 obtains the first scores.

Next, the information processing device 14 inputs the spectrogram image to a learned model that is for calculating, from the spectrogram image, second scores expressing the extents of having psychological disorders, neurological disorders or symptoms of these. Then, as illustrated in FIG. 2, the information processing device 14 obtains the second scores. The learned model is realized by, for example, a neural network that is learned by machine learning, or the like.

Next, by combining the first scores and the second scores, the information processing device 14 calculates composite scores that express the extents of the user having psychological disorders, neurological disorders or symptoms of these. Then, in accordance with the composite scores, the information processing device 14 infers whether or not the user has any disorder or symptom.

In this way, the information processing system 10 of the first embodiment infers whether or not the user has any disorder or symptom, by using not only acoustic parameters extracted from the voice data that is time series data, but also an image obtained from the voice data. Due thereto, whether or not the user has any disorder or symptom can be inferred accurately as compared with a case in which only acoustic parameters are used.

Figure 3:
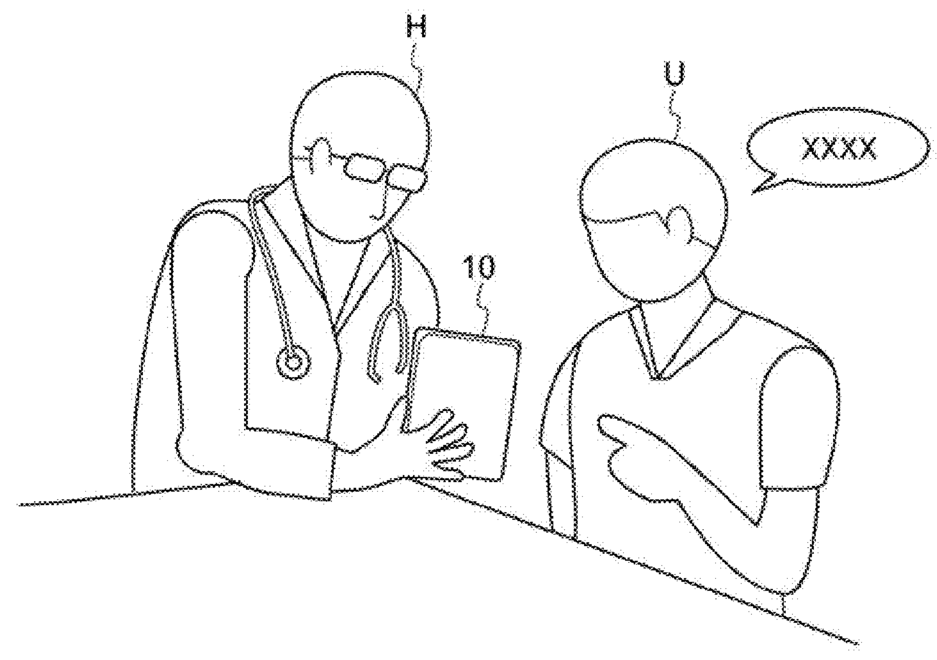
FIG. 3 is a drawing schematically illustrating an example of a form of usage of the information processing system of the first embodiment.

Usage of the information processing system 10 of the first embodiment under the conditions illustrated in FIG. 3 for example is supposed.

In the example of FIG. 3, medical worker H such as a doctor or the like holds a tablet-type terminal that is an example of the information processing system 10. The medical worker H uses the microphone (not illustrated) of the tablet-type terminal, and picks-up voice data "XXXX" of a user U who is the subject. Then, on the basis of the voice data "XXXX" of the user U, the tablet terminal infers whether or not the user U has any disorder or symptom, and outputs the results of inference to a display portion (not illustrated). The medical worker H refers to the results of inference that are displayed on the display portion (not illustrated) of the tablet terminal, and diagnoses whether or not the user U has any disorder or symptom.

Specifics are described hereinafter.

The microphone 12 picks-up voice data that is time series data of the voice uttered by the user who is the object of inferring disorders or symptom.

On the basis of the voice data picked-up by the microphone 12, the information processing device 14 infers whether or not the user has a psychological disorder, a neurological disorder or a symptom of these.

As illustrated in FIG. 1, the information processing device 14 functionally has an acquiring section 20, an extracting section 22, a generating section 24, a calculation model storage 26, a learned model storage 28, a first score calculating section 30, a second score calculating section 32, a composite score calculating section 34, and an inferring section 36. The information processing device 14 is realized by a computer such as described later.

The acquiring section 20 acquires the voice data of the user that is picked-up by the microphone 12.

The extracting section 22 extracts feature amounts, which are predetermined acoustic parameters, from the voice data acquired by the acquiring section 20. For example, the extracting section 22 extracts the following acoustic parameters, which are disclosed in International Patent Application Publication No. 2020/013296, as the feature amounts.

TABLE 1

| |
|---|
| 1) Sound volume envelope (attack time, decay time, sustain level, release time) |
| 2) Waveform variation information (shimmer, jitter) |
| 3) Zero crossing rate |
| 4) Hurst exponent |
| 5) VOT (Voice Onset Time) |
| 6) Statistical values of distribution within an utterance relating to a given mel-frequency cepstral coefficient (the first quartile, the median, the third quartile, the 95% point, the arithmetic mean, the geometric mean, the difference between the third quartile and the median, and the like) |
| 7) Statistical values of distribution within an utterance in the speed of change of the frequency spectrum (the first quartile, the median, the third quartile, the 95% point, the arithmetic mean, the geometric mean, the difference between the third quartile and the median, and the like) |
| 8) Statistical values of distribution within an utterance relating to temporal variations of a given mel-frequency cepstral coefficient (the first quartile, the median, the third quartile, the 95% point, the arithmetic mean, the geometric mean, the difference between the third quartile and the median, and the like) |
| 9) Statistical values of distribution within an utterance relating to temporal variations of temporal variations of a given mel-frequency cepstral coefficient (the first quartile, the median, the third quartile, the 95% point, the arithmetic mean, the geometric mean, the difference between the third quartile and the median, and the like) |
| 10) The square error with respect to quadratic regression approximation, in temporal variations within an utterance of the frequency spectrum of a roll-off of 90% |

TABLE 1-continued

11) The arithmetic error with respect to quadratic regression approximation, in temporal variations within an utterance of the center of gravity of the frequency spectrum. In addition, the pitch rate, the probability of being a voiced sound, the power of the frequency of an arbitrary range, the scale, the speaking speed (the number of mora in a fixed time), pause/interval, sound volume, and the like.

The generating section 24 generates a spectrogram image that expresses the spectrogram of the voice data, by carrying out frequency analysis on the voice data acquired by the acquiring section 20.

Figure 4:
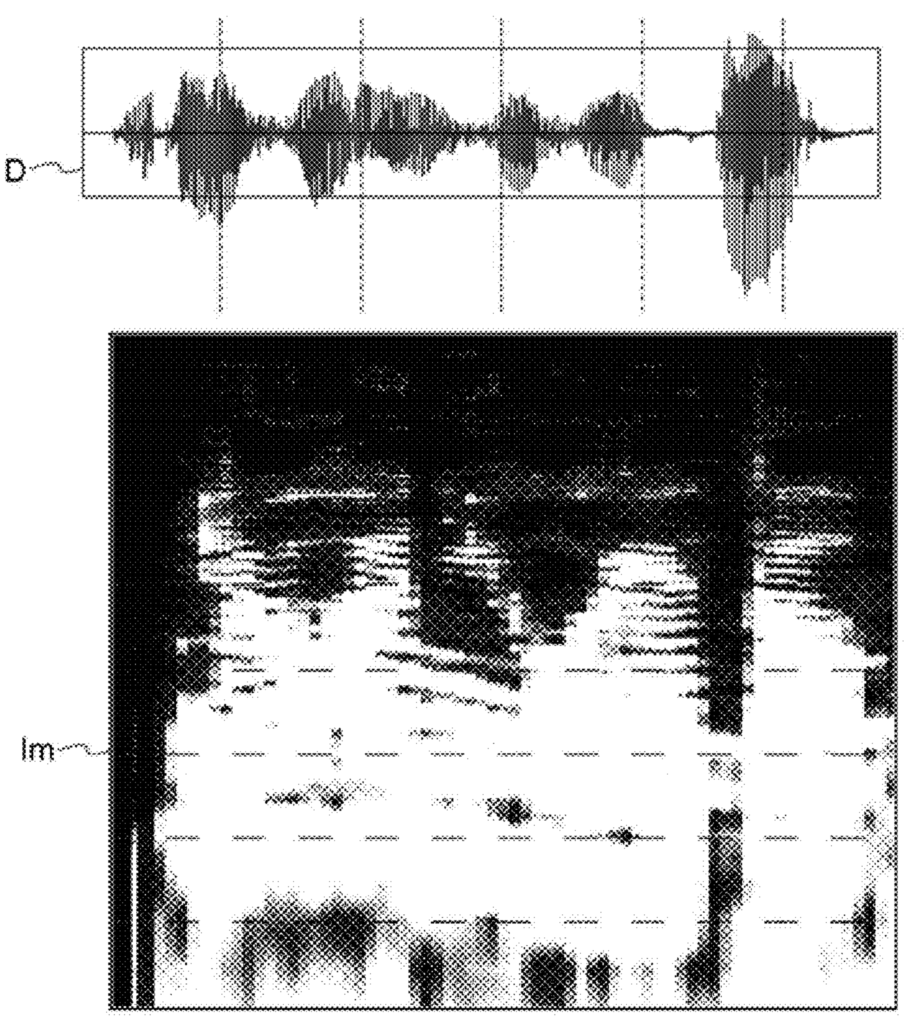
FIG. 4 is a drawing for explaining voice data and a spectrogram image.

FIG. 4 is a drawing for explaining a spectrogram image. As illustrated in FIG. 4, voice data D is time series data. The generating section 24 generates spectrogram image Im illustrated in FIG. 4 by carrying out frequency analysis on the voice data D. Note that the horizontal axis of the spectrogram image Im is the time axis, and the vertical axis of the spectrogram image Im is the frequency axis. Further, the pixel values of the spectrogram image Im correspond to the intensities of the respective frequency components. Note that, in the first embodiment, the spectrogram image is a greyscale image.

A calculation model for calculating, from the feature amounts that are acoustic parameters, scores expressing the extents of psychological disorders, neurological disorders or symptoms of these, is stored in the calculation model storage 26. The calculation model is expressed by the following calculation formulas for example.

$$F(a)=x_{a1}\times f_{a1}+x_{a2}\times f_{a2}+, \ldots, x_{an}\times f_{an} \quad (1)$$

Above formula (1) is a calculation formula for calculating a first score F(a) that expresses the extent to which the user has a given psychological disorder or symptom A. $f_{a1}, \ldots, f_{an}$ are any one or more feature amounts selected from the above-listed respective acoustic parameter items 1) through 11). Further, $x_{a1}, \ldots, x_{an}$ are coefficients that are particular to the disorder or symptom, and are set in advance.

Further, first score F(b), which expresses the extent to which the user has a given neurological disorder or symptom B, is expressed in a form that is similar to above formula (1), and is expressed by following formula (2) for example. $f_{b1}, \ldots, f_{bm}$ are any one or more feature amounts selected from the above-listed respective acoustic parameter items 1) through 11). Further, $x_{b1}, \ldots, x_{bm}$ are coefficients that are particular to the disorder or symptom, and are set in advance.

$$F(b)=x_{b1}\times f_{b1}+x_{b2}\times f_{b2}+, \ldots, x_{bm}\times f_{bm} \quad (2)$$

Further, first score F(h), which expresses the extent to which the user does not have any psychological disorder, neurological disorder or symptom of these, is expressed in a form that is similar to above formula (1), and is expressed by following formula (3) for example. $f_{h1}, \ldots, f_{hi}$ are any one or more feature amounts selected from the above-listed respective acoustic parameter items 1) through 11). Further, $x_{h1}, \ldots, x_{hi}$ are coefficients that are particular to disorders or symptoms, and are set in advance.

$$F(h)=x_{h1}\times f_{h1}+x_{h2}\times f_{h2}+, \ldots, x_{hi}\times f_{hi} \quad (3)$$

Note that there are items that are common to two or more disorders or symptoms, and a first score F(ab), which expresses the extent of having at least one of disorder or symptom A and disorder or symptom B, may be calculated by following formula (4). $f_{ab1}, \ldots, f_{abj}$ are any one or more feature amounts selected from the above-listed respective acoustic parameter items 1) through 11). $X_{ab1}, \ldots, x_{habj}$ are unique coefficients, and are set in advance.

$$F(a\ b)=x_{ab1}\times f_{ab1}+x_{ab2}\times f_{ab2}+, \ldots, x_{abj}\times f_{abj} \quad (4)$$

Further, the first score F(a) expressing the extent to which the user has disorder or symptom A, and the first score F(b) expressing the extent to which the user has disorder or symptom B, may respectively be calculated from following formulas (5) (6) by using the first score F(ab) that expresses the extent of having at least one of disorder or symptom A and disorder or symptom B.

$$F(a)=F(a\ b)+x_{a1}\times f_{a1}+x_{a2}\times f_{a2}+, \ldots, x_{an}\times f_{an} \quad (5)$$

$$F(b)=F(a\ b)+x_{b1}\times f_{b1}+x_{b2}\times f_{b2}+, \ldots, x_{bm}\times f_{bm} \quad (6)$$

A learned model, which has been machine-learned in advance and is for calculating, from the spectrogram image, scores expressing the extents of psychological disorders, neurological disorders or symptoms of these, is stored in the learned model storage 28.

Figure 5:
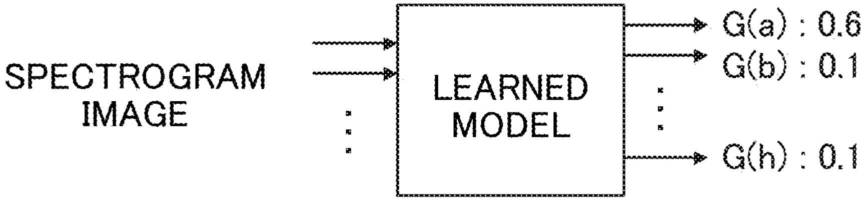
FIG. 5 is a drawing for explaining a learned model.

A drawing for explaining the learned model is illustrated in FIG. 5. As illustrated in FIG. 5, when pixel values of respective places of the spectrogram image are inputted into the learned model, second scores expressing the extents of psychological disorders, neurological disorders, or symptoms of these are outputted from the learned model.

In the example illustrated in FIG. 5, second score G(a): 0.6 expressing the extent to which the user has disorder or symptom A, second score G(b): 0.1 expressing the extent to which the user has disorder or symptom B, and second score G(h): 0.1 expressing the extent to which the user does not have any disorder or symptom are outputted from the learned model.

The learned model is machine-learned in advance by teacher data that is set in advance. The learned model may be any type of model, provided that it is a model that can be learned by machine learning. FIG. 6 is a drawing for explaining teacher data. As illustrated in FIG. 6, for example, the teacher data is data in which spectrogram images for learning, and correct answer labels expressing disorders or symptoms of users who uttered the voice data corresponding to those spectrogram images for learning, are set in correspondence with one another.

The first score calculating section 30 calculates the first scores, which express the extents to which the user has psychological disorders, neurological disorders or symptoms of these, on the basis of feature amounts extracted by the extracting section 22 and calculation formulas stored in the calculation model storage 26.

Specifically, the first score calculating section 30 reads-out calculation formulas stored in the calculation model storage 26, and inputs the values of the feature amounts extracted by the extracting section 22 into the feature amount portions of these calculation formulas, and calculates the first scores.

For example, by inputting the values of the feature amounts into the calculation formulas, the first score calculating section 30 calculates the first score F(a) expressing the extent to which the user has a given psychological disorder or symptom A, the first score F(b) expressing the extent to which the user has a given neurological disorder or symptom B, and the first score F(h) expressing the extent to which the user does not have any disorder or symptom. Note that the first score F(a) is an example of a first psychological disorder score expressing the extent to which the user has a psychological disorder or a symptom thereof. Further, the first score F(b) is an example of a first neurological disorder score expressing the extent to which the user has a neurological disorder or a symptom thereof. Further, the first score F(h) is an example of a first healthy score expressing the extent to which the user does not have any psychological disorder, neurological disorder or symptom of these.

The second score calculating section 32 inputs the spectrogram image that was generated by the generating section 24 into the learned model stored in the learned model storage 28, and calculates the second scores expressing the extents to which the user has psychological disorders, neurological disorders or symptoms of these.

For example, by inputting the respective pixel values of the spectrogram image into the learned model, the second score calculating section 32 calculates the second score G(a) expressing the extent to which the user has a given psychological disorder or symptom A, the second score G(b) expressing the extent to which the user has a given neurological disorder or symptom B, and the second score G(h) expressing the extent to which the user does not have any disorder or symptom. Note that the second score G(a) is an example of a second psychological disorder score expressing the extent to which the user has a psychological disorder or a symptom thereof. Further, the second score G(b) is an example of a second neurological disorder score expressing the extent to which the user has a neurological disorder or a symptom thereof. Further, the second score G(h) is an example of a second healthy score expressing the extent to which the user does not have any psychological disorder, neurological disorder or symptom of these.

Note that the second score calculating section 32 adjusts the size of the spectrogram image in accordance with the length of the voice data.

For example, in a case in which the user is asked to utter plural phrases that are set in advance and are for inferring whether or not there is a disorder or symptom, the length of that voice data in the time axis direction differs per phrase. For example, the lengths of the phrase "I'm hungry" and the phrase "The weather is nice today" are different, and the spectrogram images generated from the voice data of these respective phrases also are different sizes.

Thus, at the time of inputting a spectrogram image into the learned model, the second score calculating section 32 adjusts the size of the spectrogram image.

Specifically, in a case in which the size of the spectrogram image that is the object of input is larger than the size of the input layer of the learned model, the second score calculating section 32 sets a random cutting position in the spectrogram image, and cuts an image out in accordance with that cutting position. Then, the second score calculating section 32 inputs the cut-out spectrogram image into the learned model, and calculates the second scores.

On the other hand, in a case in which the size of the spectrogram image that is the object of input is smaller than the size of the input layer of the learned model, the second score calculating section 32 inserts black frames at a random width in both sides of the spectrogram image. Then, the second score calculating section 32 inputs the spectrogram image, into which the black frames have been inserted, into the learned model, and calculates the second scores.

Note that, at the time of learning a model as well, the size of the spectrogram image is adjusted by such techniques. Note that, when black frames are inserted at a random width in both sides of the spectrogram image at the time of learning, there are cases in which learning does not go well, and therefore, an average image of all of the spectrogram images for learning is generated, and that average image is inserted in the both sides of the object spectrogram image. Note that, in this case, the insertion width of the average image into both sides of the image, and the cutting position of an image that is larger than the input size, are changed randomly each time that a weighting parameter of the intermediate layer of the model is changed slightly by updated learning. Due thereto, the performance of the learned model can be improved.

By combining the first scores calculated by the first score calculating section 30 and the second scores calculated by the second score calculating section 32, the composite score calculating section 34 calculates composite scores expressing the extents to which the user has psychological disorders, neurological disorders or symptoms of these. For example, the composite score calculating section 34 calculates the sum of the first score and the second score as a composite score.

For example, by adding the first score F(a) and the second score G(a), the composite score calculating section 34 calculates composite score S(a) expressing the extent to which the user has the given psychological disorder or symptom A. Further, by adding the first score F(b) and the second score G(b), the composite score calculating section 34 calculates composite score S(b) expressing the extent to which the user has the given neurological disorder or symptom B. Further, by adding the first score F(h) and the second score G(h), the composite score calculating section 34 calculates composite score S(h) expressing the extent to which the user does not have any disorder or symptom.

In accordance with the composite scores calculated by the composite score calculating section 34, the inferring section 36 infers whether or not the user has any disorder or symptom. For example, the inferring section 36 infers that the user has the disorder or symptom whose composite score is the highest. Or, for example, the inferring section 36 infers that the user has the disorder or symptom whose composite score is greater than or equal to a predetermined threshold value. For example, in a case in which the disorders or symptoms whose composite scores are greater than or equal to predetermined threshold values are psychological disorder or symptom A and neurological disorder or symptom B, the inferring section 36 infers that the user has both psychological disorder or symptom A and neurological disorder or symptom B. Further, for example, in a case in which the composite score S(h) is the highest, the inferring section 36 infers that the user does not have a disorder or symptom.

The inferring section 36 outputs the results of inference relating to the absence/presence of disorders or symptoms of the user. Note that the inferring section 36 may output the composite scores of the respective disorders or symptoms themselves as the results of inference.

The display device 16 displays the results of inference that are outputted from the inferring section 36.

The medical worker who operates the information processing device 14 or the user confirms the results of inference that are outputted from the display device 16, and confirms what kinds of disorders or symptoms there is the possibility the user may have.

Figure 7:
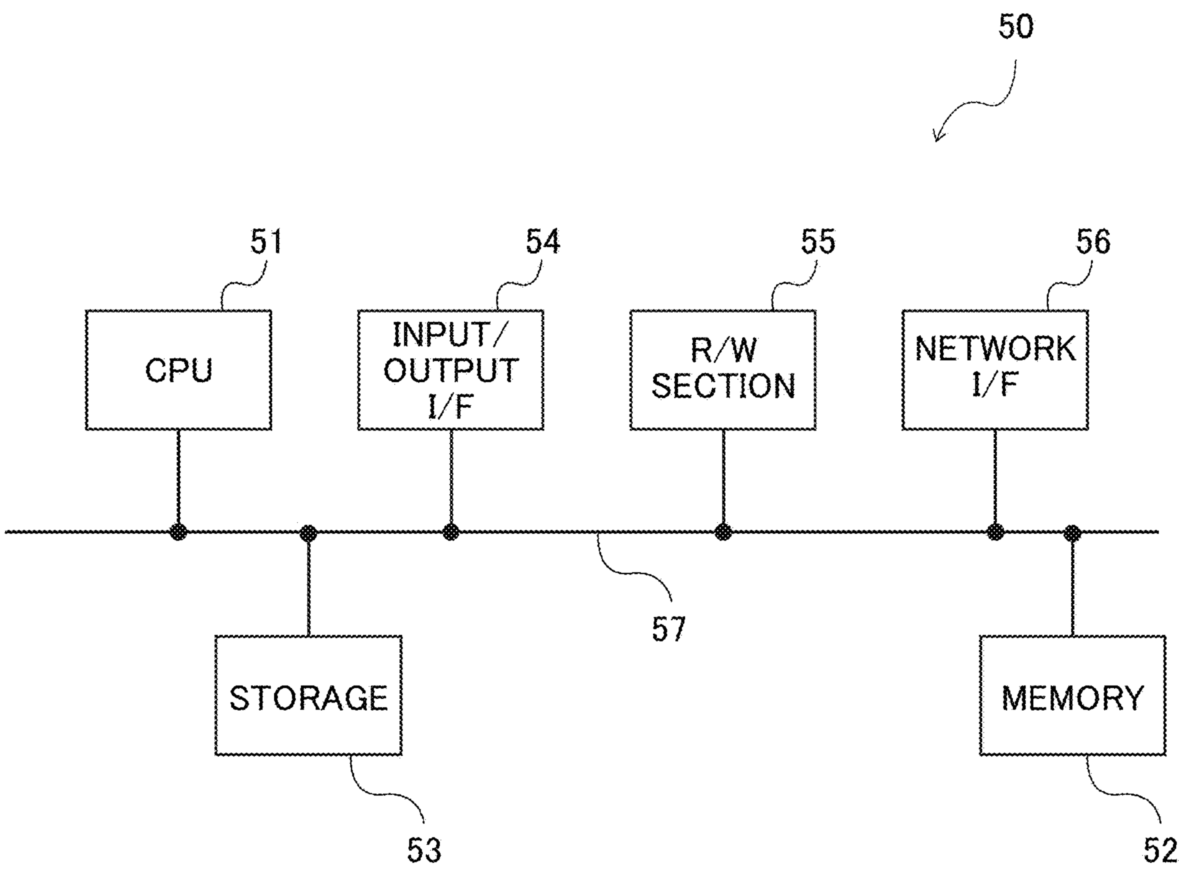
FIG. 7 is a drawing illustrating an example of a computer that structures an information processing device.

The information processing device 14 can be realized by a computer 50 illustrated in FIG. 7 for example. The computer 50 has a CPU 51, a memory 52 serving as a temporary storage region, and a non-volatile storage 53. Further, the computer 50 has an input/output interface (I/F) 54 to which external devices and output devices and the like are connected, and a read/write (R/W) section 55 that controls the reading and writing of data from and to recording media. Further, the computer 50 has a network I/F 56 that is connected to a network such as the internet or the like. The CPU 51, the memory 52, the storage 53, the input/output I/F 54, the R/W section 55, and the network I/F 56 are connected to one another via bus 57.

The storage 53 can be realized by a Hard Disk Drive (HDD), a Solid State Drive (SSD), a flash memory, or the like. A program for making the computer 50 function is stored in the storage 53 that serves as a storage medium. The CPU 51 reads-out the program from the storage 53 and expands the program in the memory 52, and successively executes the processes that the program has.

[Operation of Information Processing System of First Embodiment]

Figure 8:
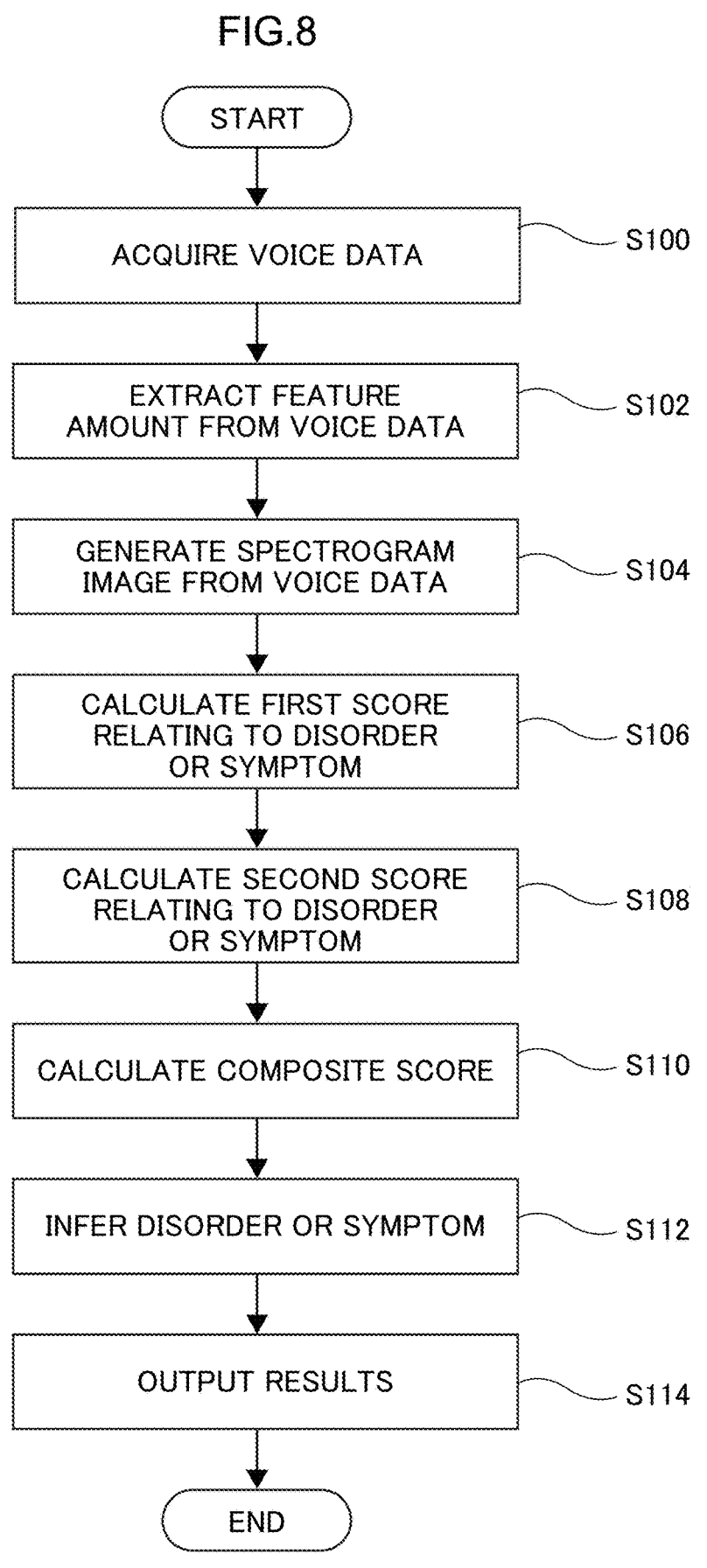

Specific operation of the information processing system 10 of the first embodiment is described next. The information processing device 14 of the information processing system 10 executes the respective processings shown in FIG. 8.

First, in step S100, voice data of the user that has been picked-up by the microphone 12 is acquired.

Next, in step S102, the extracting section 22 extracts predetermined acoustic parameters such as disclosed in International Patent Application Publication No. 2020/013296, as feature amounts from the voice data acquired in above step S100.

In step S104, by carrying out frequency analysis on the voice data acquired in above step S100, the generating section 24 generates a spectrogram image expressing the spectrogram of the voice data.

In step S106, on the basis of feature amounts extracted in above step S102 and calculation formulas stored in the calculation model storage 26, the first score calculating section 30 calculates the first scores that express the extents to which the user has psychological disorders, neurological disorders or symptoms of these.

In step S108, the second score calculating section 32 inputs the spectrogram image generated in above step S104 to the learned model stored in the learned model storage 28, and calculates the second scores expressing the extents to which the user has psychological disorders, neurological disorders or symptoms of these.

In step S110, by combining the first scores calculated in above step S106 and the second scores calculated in above step S108, the composite score calculating section 34 calculates composite scores expressing the extents to which the user has psychological disorders, neurological disorders or symptoms of these.

In step S112, in accordance with the composite scores calculated in above step S110, the inferring section 36 infers whether or not the user has any disorder or symptom.

In step S114, the inferring section 36 outputs the results of inference that were obtained in above step S112.

The display device 16 displays the results of inference that were outputted from the inferring section 36. The medical worker who operates the information processing device 14 or the user confirms the results of inference that were outputted from the display device 16, and confirms what kinds of disorders or symptoms there is the possibility the user may have.

As described above, the information processing system 10 of the first embodiment acquires voice data, which is time series data of a voice the user uttered, and extracts a feature amount that is a predetermined acoustic parameter from the voice data. Then, by carrying out frequency analysis on the acquired voice data, the information processing system 10 generates a spectrogram image that expresses the spectrogram of the voice data. On the basis of the feature amount, and a calculation model that is set in advance for calculating, from the feature amount, a score expressing the extent of a psychological disorder, a neurological disorder or a symptom of these, the information processing system 10 calculates a first score expressing the extent to which the user has a psychological disorder, a neurological disorder or a symptom of these. The information processing system 10 inputs the spectrogram image into a learned model that has been learned in advance and is for calculating, from the spectrogram image, a score expressing the extent of a psychological disorder, a neurological disorder or a symptom of these, and calculates a second score that expresses the extent to which the user has a psychological disorder, a neurological disorder or a symptom of these. By combining the first score and the second score, the information processing system 10 calculates a composite score expressing the extent to which the user has a psychological disorder, a neurological disorder or a symptom of these. Then, in accordance with the composite score, the information processing system 10 infers whether or not the user has any disorder or symptom. Due thereto, the information processing system 10 can accurately infer whether or not the user has a psychological disorder, a neurological disorder or a symptom of these, as compared with a case of inferring a psychological disorder, a neurological disorder or a symptom of these by using parameters extracted from the time series data of the voice the user uttered. More specifically, a disorder or symptom of the user can be inferred more accurately by inferring the disorder or symptom by using a spectrogram image obtained from voice data, in addition to conventional acoustic parameters.

Further, at the time of calculating the score of a disorder or symptom of a user from a spectrogram image, the second score can be calculated easily from the spectrogram image by using a learned model. Further, at the time of inputting spectrogram images into the learned model, phrases of differing lengths can also be handled by adjusting the sizes of the spectrogram images.

<Information Processing System of Second Embodiment>

A second embodiment is described next. Note that, because the structure of the information processing system of the second embodiment is a structure similar to that of the first embodiment, the same reference numerals are applied, and description is omitted.

The information processing system of the second embodiment differs from the first embodiment with regard to the point that a learned model such as a neural network or the like is used also at the time of calculating the first scores from the feature amounts that are acoustic parameters.

Figure 9:
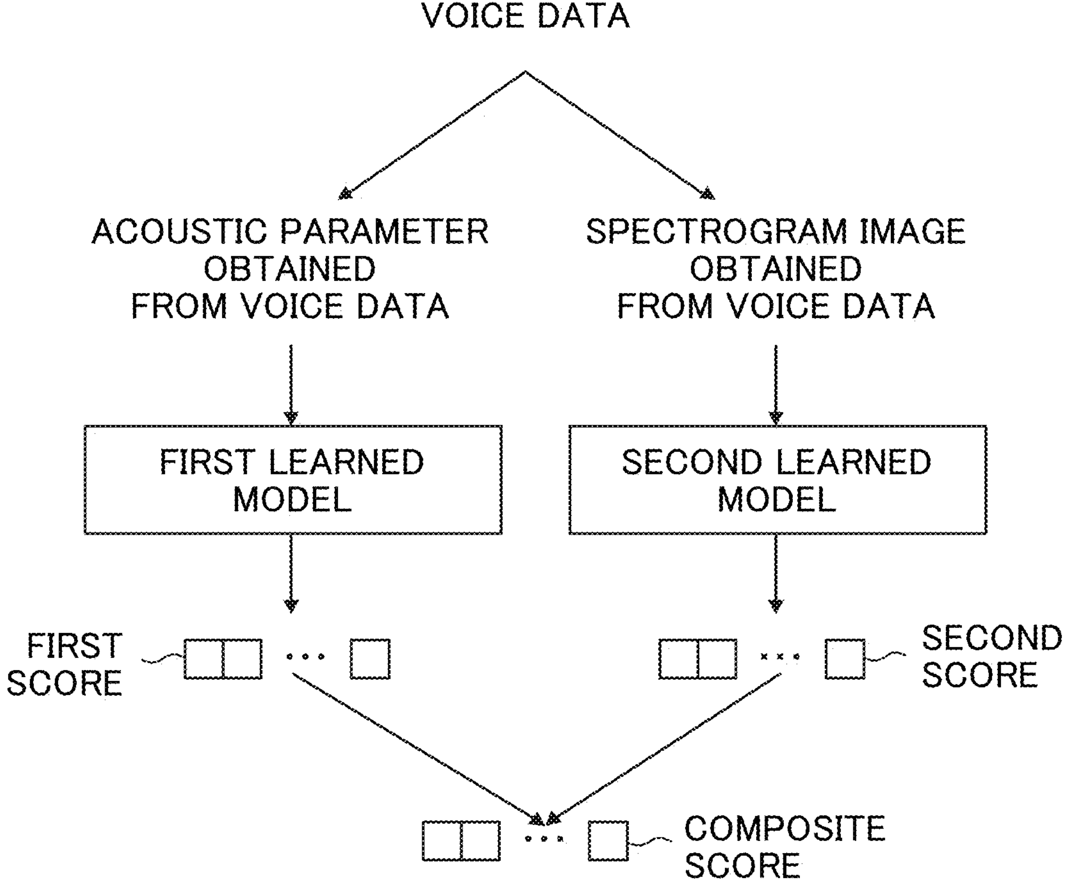
FIG. 9 is a drawing for explaining an overview of a second embodiment.

A drawing for explaining an overview of the information processing system 10 of the second embodiment is illustrated in FIG. 9. The information processing system 10 of the second embodiment uses a first learned model such as a neural network or the like as the calculation model of the first embodiment.

Specifically, as illustrated in FIG. 9, the information processing device 14 of the information processing system 10 of the second embodiment inputs feature amounts that are acoustic parameters into the first learned model that is a calculation model for calculating, from the feature amounts, the first scores expressing the extents of having psychological disorders, neurological disorders or symptoms of these. Further, the information processing device 14 of the information processing system 10 of the second embodiment uses the scores that are outputted from the first learned model as the first scores.

Note that the learned model of the first embodiment corresponds to the second learned model illustrated in FIG. 9. Therefore, when a spectrogram image is inputted into the second learned model, the second scores are outputted from the second learned model.

Specifics are described hereinafter.

The first learned model of the second embodiment is realized by a known neural network or the like. The first learned model is machine-learned in advance by teacher data that is set in advance. FIG. 10 is a drawing for explaining the teacher data that is used at the time of learning the first learned model. As illustrated in FIG. 10, for example, the teacher data is data in which feature amount groups for learning, and correct answer labels expressing disorders or symptoms of users who uttered the voice data from which those feature amount groups were obtained, are set in correspondence with one another.

Because the other structures and operations of the information processing system of the second embodiment are similar to those of the first embodiment, description thereof is omitted.

As described above, the information processing system of the second embodiment uses the first learned model which is learned in advance and is for calculating a score expressing a psychological disorder, a neurological disorder or a symptom of these from a feature amount that is an acoustic parameter. Specifically, the information processing system of the second embodiment inputs a feature amount, which is extracted from voice data of the user, into the first learned model, and calculates the first score. Then, the information processing system of the second embodiment inputs the spectrogram image into the second learned model, and calculates the second score. By combining the first score and the second score, the information processing system of the second embodiment calculates a composite score expressing the extent to which the user has a psychological disorder, a neurological disorder or a symptom of these. Then, in accordance with the composite score, the information processing system of the second embodiment infers whether or not the user has any disorder or symptom. Due thereto, the information processing system of the second embodiment can accurately infer whether or not the user has a psychological disorder, a neurological disorder or a symptom of these, as compared with a case of inferring a psychological disorder, a neurological disorder or a symptom of these by using parameters extracted from the time series data of the voice the user uttered.

<Information Processing System of Third Embodiment>

A third embodiment is described next. Note that, among the structures of the information processing system of the third embodiment, portions that are structured similarly to the first embodiment or second embodiment are denoted by the same reference numerals, and description thereof is omitted.

Figure 11:
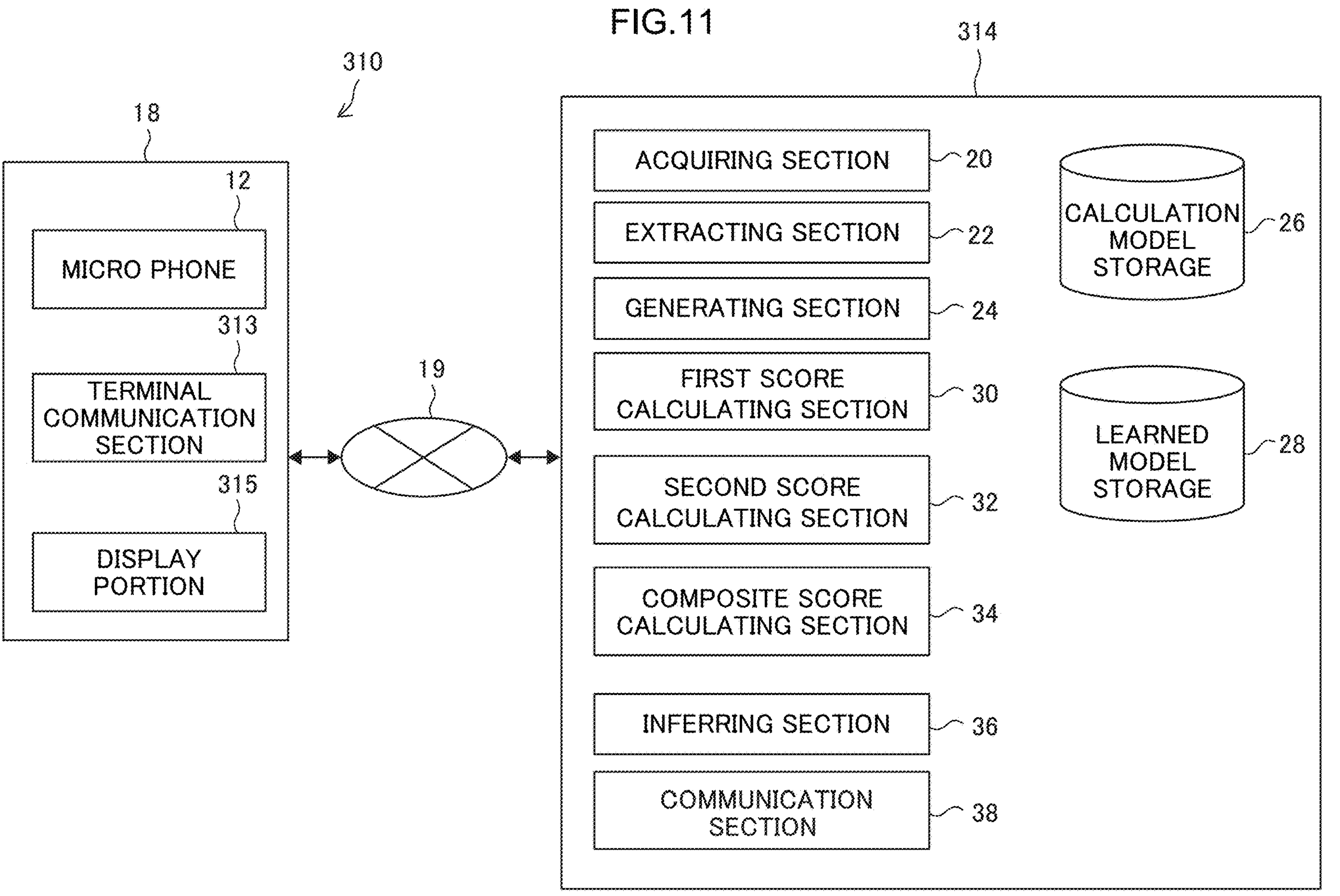
FIG. 11 is a drawing illustrating an example of the schematic structure of an information processing system of a third embodiment.

An information processing system 310 relating to the third embodiment is illustrated in FIG. 11. As illustrated in FIG. 11, the information processing system 310 of the third embodiment has a user terminal 18 and an information processing device 314.

On the basis of the voice of the user that is picked-up by the microphone 12 of the user terminal 18, the information processing device 314 of the information processing system 310 infers whether or not a user has a psychological disorder, a neurological disorder or a symptom of these.

Figure 12:
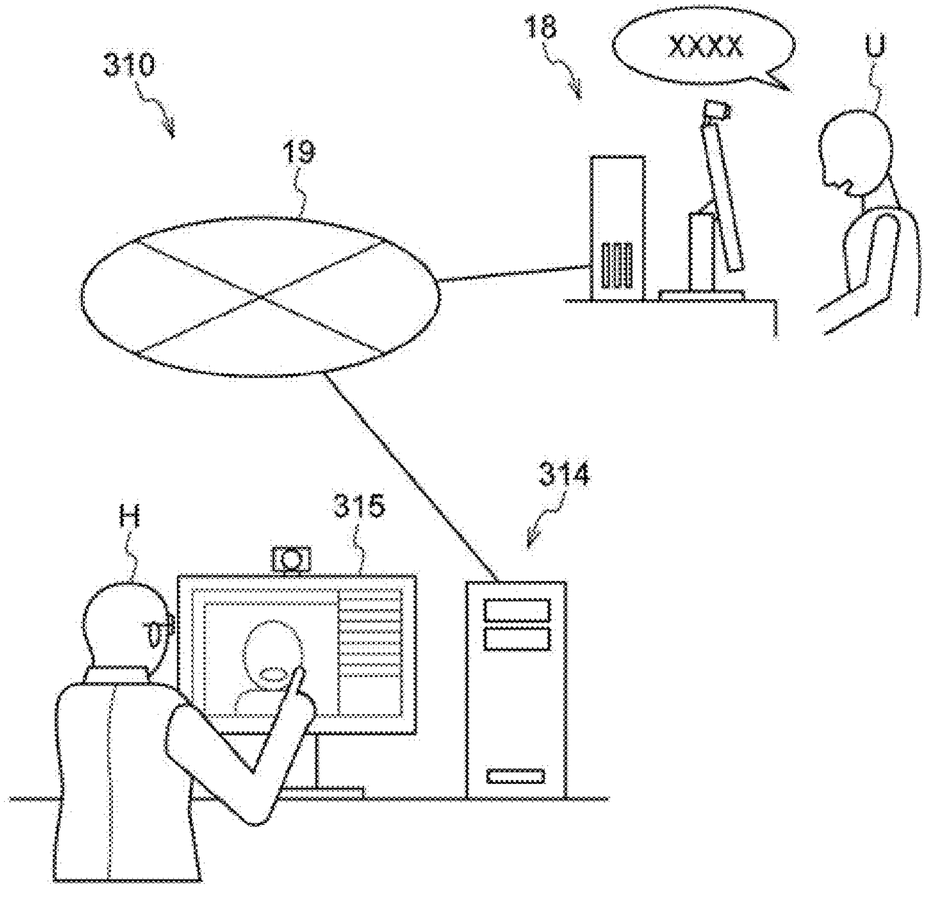
FIG. 12 is a drawing schematically illustrating an example of a form of usage of the information processing system of the third embodiment.
Figure 13:
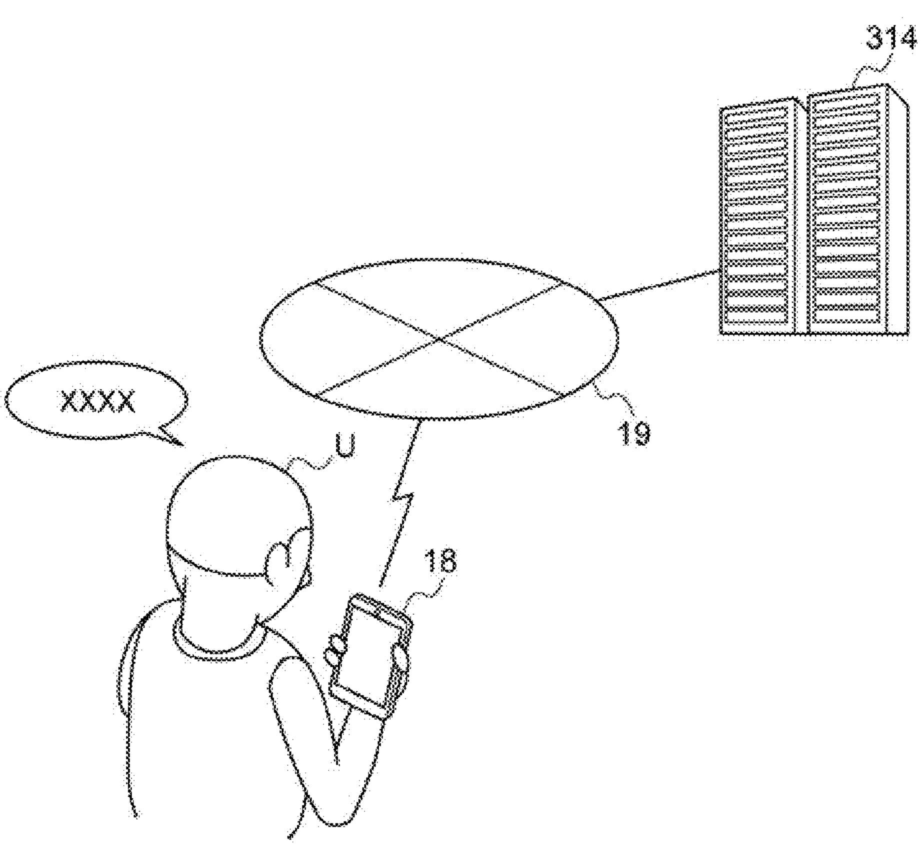
FIG. 13 is a drawing schematically illustrating an example of a form of usage of the information processing system of the third embodiment.

Usage of the information processing system 310 of the third embodiment under the conditions illustrated in FIG. 12 and FIG. 13 for example is supposed.

In the example of FIG. 12, the medical worker H such as a doctor or the like operates the information processing device 314, and the user U who is the subject operates the user terminal 18. The user U picks-up his/her own voice data "XXXX" by the microphone 12 of the user terminal 18 that he/she is operating. Then, the user terminal 18 transmits the voice data to the information processing device 314 via a network 19 such as the internet or the like.

The image processing device 314 receives the voice data "XXX" of the user U that was transmitted from the user terminal 18. Then, on the basis of the received voice data, the information processing device 314 infers whether or not the user U has any disorder or symptom, and outputs the results of inference to a display portion 315 of the information processing device 314. The medical worker H refers to the results of inference that are displayed on the display portion 315 of the information processing device 314, and diagnoses whether or not the user U has any disorder or symptom.

On the other hand, in the example of FIG. 13, the user U who is the subject picks-up his/her own voice data "XXXX" by the microphone 12 of the user terminal 18 that he/she is operating. Then, the user terminal 18 transmits the voice data to the information processing device 314 via the network 19 such as the internet or the like. The information processing device 314 receives the voice data "XXX" of the user U transmitted from the user terminal 18. Then, on the basis of the received voice data, the information processing device 314 infers whether or not the user U has any disorder or symptom, and transmits the results of inference to the user terminal 18. The user terminal 18 receives the results of inference that were transmitted from the information processing device 14, and displays the results of inference on a display portion (not illustrated). The user confirms the results of inference, and confirms what kinds of disorders or symptoms there is the strong possibility that he/she may have.

[Operation of Information Processing System of Third Embodiment]

Specific operation of the information processing system 310 of the third embodiment is described. The user terminal 18 and the information processing device 314 of the information processing system 310 execute the respective processings shown in FIG. 14.

First, in step S200, a terminal communication section 313 of the user terminal 18 acquires voice data of the user that has been picked-up by the microphone 12.

In step S202, the terminal communication section 313 of the user terminal 18 transmits the voice data acquired in above step S200 to the information processing device 314 via the network 19.

In step S203, the communication section 38 of the information processing device 314 receives the voice data transmitted from the user terminal 18.

Figure 14:
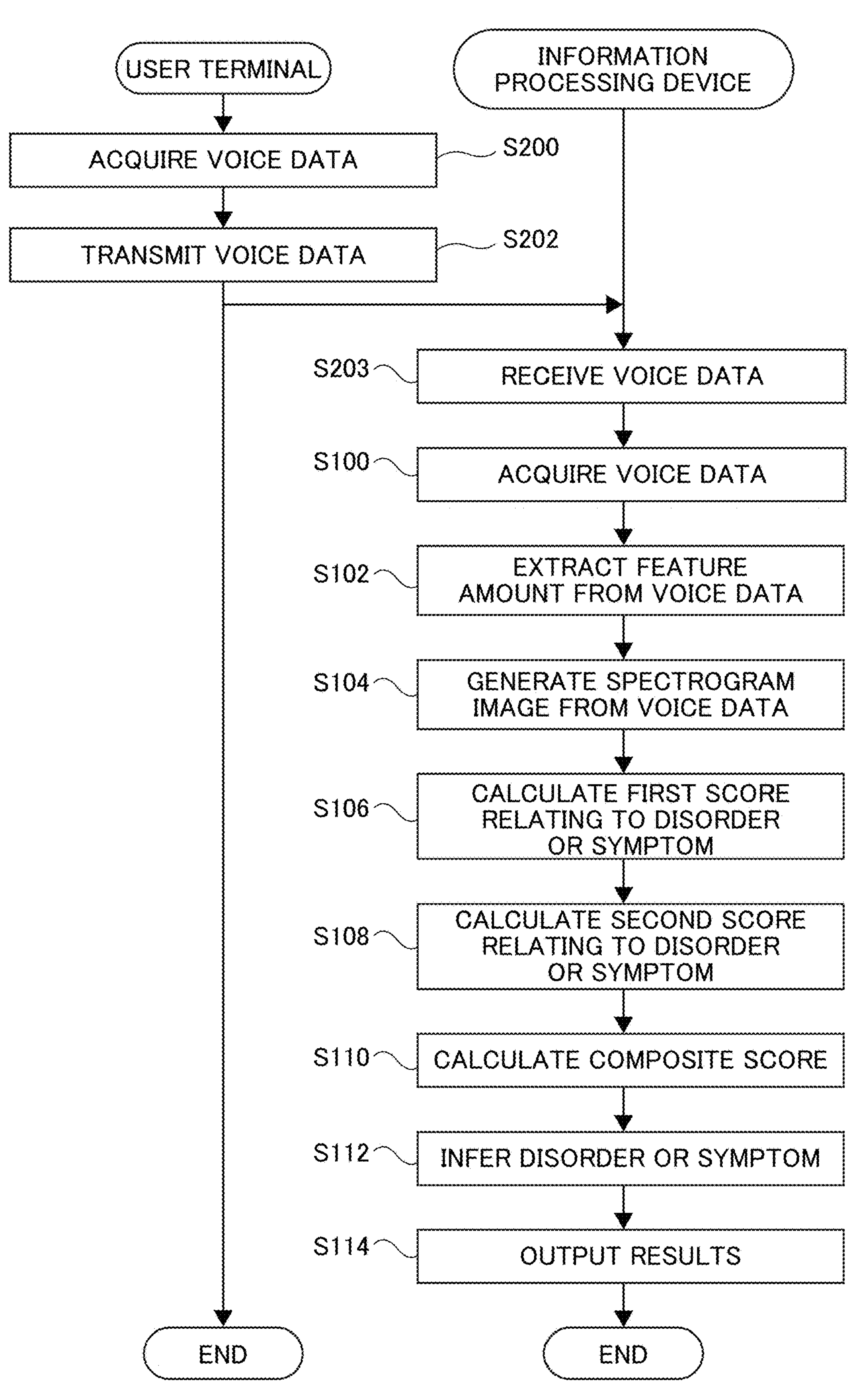
FIG. 14 is a drawing illustrating an example of processings executed by a user terminal and an information processing device of the third embodiment.

The respective processings of step S100 through step S114 of FIG. 14 are executed similarly to the information processing system 10 of the first embodiment.

Note that the results of inference that are outputted in step S114 may be transmitted to the user terminal 18, or may be displayed on a display device (not illustrated) of the information processing device 14.

Because the other structures and operations of the information processing system of the third embodiment are similar to those of the first or second embodiment, description thereof is omitted.

As described above, the information processing system of the third embodiment can infer whether or not the user has a psychological disorder, a neurological disorder or a symptom of these, by using the information processing device 14 that is set in the cloud.

<Information Processing System of Fourth Embodiment>

A fourth embodiment is described next. Note that, among the structures of the information processing system of the fourth embodiment, portions that are structured similarly to the first through third embodiments are denoted by the same reference numerals, and description thereof is omitted.

Figure 15:
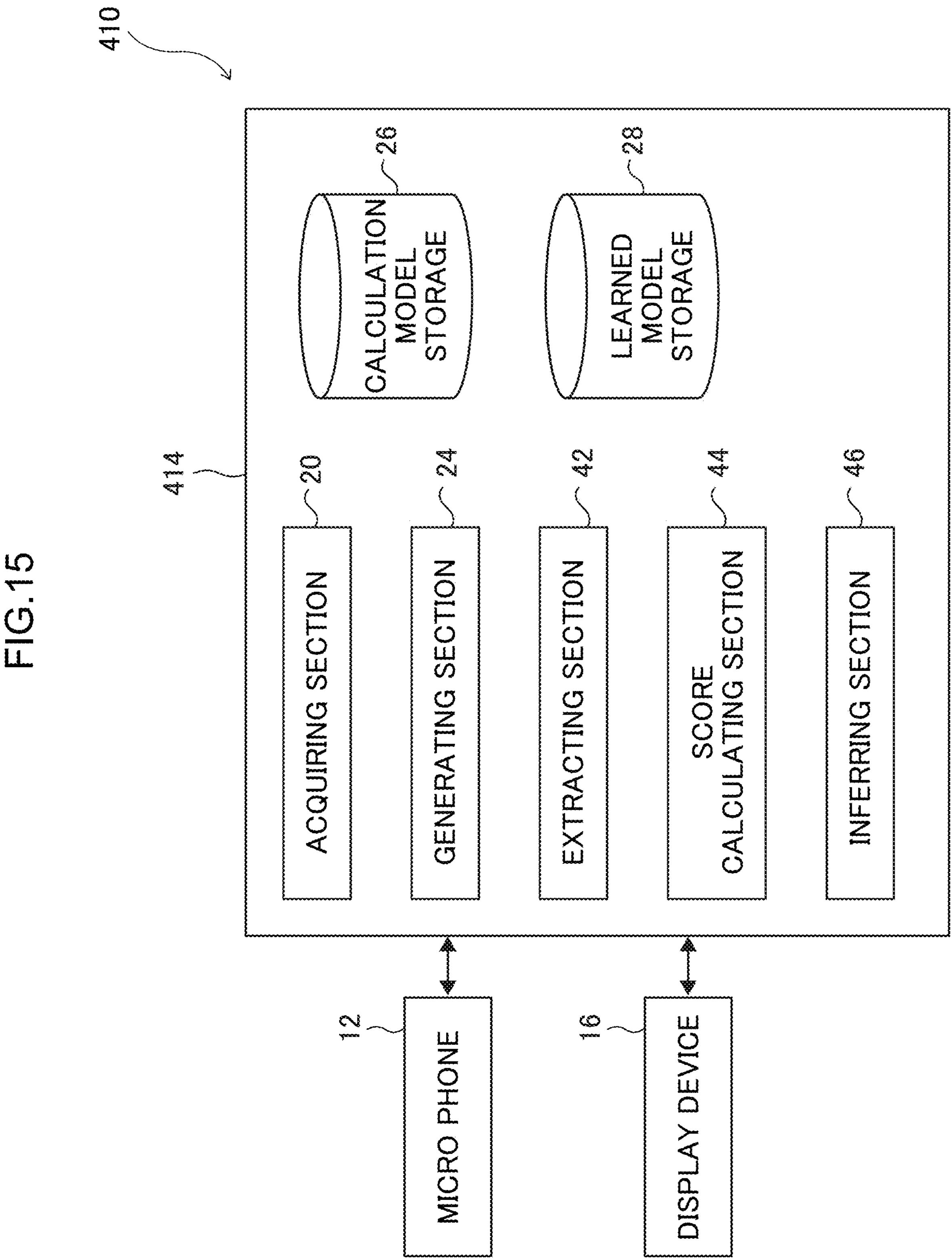
FIG. 15 is a drawing illustrating an example of the schematic structure of an information processing system of a fourth embodiment.

An information processing system 410 relating to the fourth embodiment is illustrated in FIG. 15. As illustrated in FIG. 15, the information processing device 414 of the information processing system 410 of the third embodiment functionally has the acquiring section 20, the generating section 24, an extracting section 42, a score calculating section 44, and an inferring section 46.

In the same way as in the first through third embodiments, the extracting section 42 of the fourth embodiment extracts predetermined acoustic parameters as feature amounts from voice data. Moreover, the extracting section 42 of the fourth embodiment extracts feature amounts also from the spectrogram image generated by the generating section 24.

Specifically, by using the learned model stored in the learned model storage 28, the extracting section 42 extracts feature amounts from the spectrogram image generated by the generating section 24.

Figure 16:
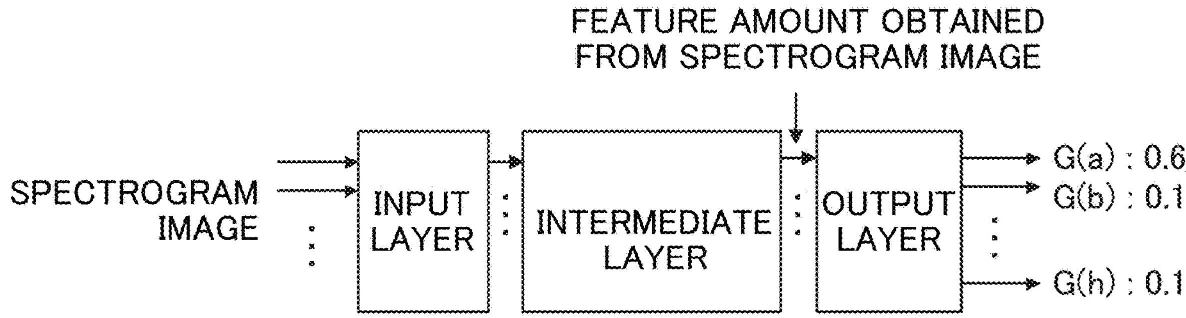
FIG. 16 is a drawing for explaining a feature amount obtained from a learned model.

FIG. 16 is a drawing for explaining the extracting of feature amounts by using the learned model. As illustrated in FIG. 16, the learned model is structured to include an input layer, an intermediate layer, and an output layer. Values of the layer before the output (values outputted from the intermediate layer) can be utilized as the feature amounts as well.

Thus, the extracting section 42 of the fourth embodiment inputs respective pixel values of the spectrogram image to the learned model, and extracts values, which are outputted from the intermediate layer of the learned model, as the feature amounts.

On the basis of the feature amounts extracted by the extracting section 42 and the calculation model stored in the calculation model storage 26, the score calculating section 44 calculates scores expressing the extents to which the user has psychological disorders, neurological disorders or symptoms of these.

For example, following formula (7) or the like can be used as the calculation formula that is an example of the calculation model of the fourth embodiment. Note that the score F(a) calculated from the following formula expresses the extent to which the user has disorder or symptom A. Note that $x_{an}$, $y_{am}$ are fixed coefficients and are set in advance. These coefficients $x_{an}$, $y_{am}$ are determined by, for example, machine learning or regression analysis or the like. f is a first feature amount expressing an acoustic parameter extracted from the voice data, and g is a second feature amount extracted from the spectrogram image by using the learned model.

$$F(a)=x_{a1}\times f(1)+, \ldots x_{an}\times f(n)+y_{a1}\times g(1)+, \ldots ,y_{am}\times g(m) \quad (7)$$

In accordance with the score calculated by the score calculating section 44, the inferring section 46 infers whether or not the user has any disorder or symptom.

Because the other structures and operations of the information processing system of the fourth embodiment are similar to those of the first through second embodiments, description thereof is omitted.

The information processing system 410 of the fourth embodiment extracts a feature amount that is a predetermined acoustic parameter from voice data, and extracts a feature amount from a spectrogram image by using a learned model. Then, on the basis of the feature amounts, and a calculation model that is set in advance and is for calculating a score expressing the extent of a psychological disorder, a neurological disorder or a symptom of these from these feature amounts, the information processing system 410 calculates a score expressing the extent to which the user has a psychological disorder, a neurological disorder or a symptom of these. Then, in accordance with the score, the information processing system 410 infers whether or not the user has any disorder or symptom. Note that the learned model is a learned model that has been learned in advance from teacher data in which spectrogram images for learning and correct answer labels expressing disorders or symptoms of users who uttered the voice data corresponding to those spectrogram images for learning, are set in correspondence with one another. Due thereto, the information processing system of the fourth embodiment can accurately infer whether or not the user has a psychological disorder, a neurological disorder or a symptom of these, as compared with a case of inferring a psychological disorder, a neurological disorder or a symptom of these by using parameters extracted from the time series data of the voice the user uttered.

Further, the learned model that is used at the time of extracting feature amounts from the spectrogram image is learned on the basis of teacher data in which spectrogram images for learning and correct answer labels relating to disorders or symptoms are set in correspondence with one another. Therefore, feature amounts for accurately inferring disorder or symptoms of the user can be extracted.

Example 1

Example 1 is described next. In Example 1, the subject utters 24 phrases, and voice data obtained from these utterances is collected. Then, inferring of disorders or symptoms of the subject is carried out by using various techniques and on the basis of these voice data.

Note that ResNet, which is a known neural network disclosed in the following reference publication, is used as an example of the learned model at the time of calculating the first score.

Reference Document: K. He, X. Zhang, S. Ren, and J. Sun. "Deep residual learning for image recognition.", In Proc. of CVPR, 2016.

Further, the linear equations expressed by above formula (1) through formula (6) are used as the calculation model at the time of calculating the second score.

The test results are shown in FIG. 17. The test results of FIG. 17 are test results of a case in which plural subjects are asked to utter 24 phrases (Ph.01 through Ph.024), and disorders or symptoms of the subjects are inferred on the basis of these voice data.

Note that "CI" that is used hereinafter corresponds to a group of cognitive impairments, and means neurological disorders or symptoms of cognitive impairments. The group of cognitive impairments includes, for example, Alzheimer's dementia, Lewy body dementia, mild cognitive impairment, frontotemporal dementia, vascular dementia, early-onset dementia, alcohol-related dementia, corticobasal degeneration syndrome, argyrophilic grain dementia, hydrocephaly, disorders presenting symptoms of other cognitive impairments, or cognitive impairment symptoms. Further, "MDs" corresponds to a group of psychological disorders, and means psychological disorders or symptoms of psychological disturbances. The group of psychological disorders includes major depression, bipolar depression, nonspecific depression, cyclothymia, dysthymia, schizophrenia, and other psychological disorders or psychological disturbance symptoms. "CTRL" means not having any psychological disorder, neurological disorder, or symptom of these.

The test results of FIG. 17 are results inferring whether or not a subject is "CI". Note that "others" means that the subject is other than "CI".

The row "inference from first scores" is the correct answer rate per phrase in cases in which disorders or symptoms are inferred by using only the first scores which are calculated from predetermined calculation formulas by using acoustic parameters as the feature amounts, in the above-described embodiments. Further, the row "inference from second scores" is the correct answer rate per phrase in cases in which disorders or symptoms are inferred by using only the second scores that are calculated from the learned ResNet, in the above-described embodiments.

As illustrated in FIG. 17, there are more phrases with a high correct answer rate in cases of using the second scores than in cases of using only the first scores. Further, it can be understood that, in cases of using the composite scores that are obtained by combining by adding the first scores and the second scores, there are phrases having even higher correct answer rates.

The following table shows the false-positive rates and the positive rates in cases of inferring whether or not a subject is "CI" by using composite scores and respective threshold values. Further, an ROC curve prepared by using the numerical values of the following table is shown in FIG. 18.

TABLE 2

| threshold value | false positive | positive |
|---|---|---|
| 0.259 | 0.11 | 0.96 |
| 0.272 | 0.09 | 0.96 |
| 0.285 | 0.065 | 0.96 |
| 0.298 | 0.058 | 0.944 |
| 0.319 | 0.052 | 0.944 |
| 0.347 | 0.052 | 0.928 |
| 0.363 | 0.045 | 0.92 |
| 0.376 | 0.045 | 0.904 |
| 0.388 | 0.032 | 0.896 |

Figure 18:
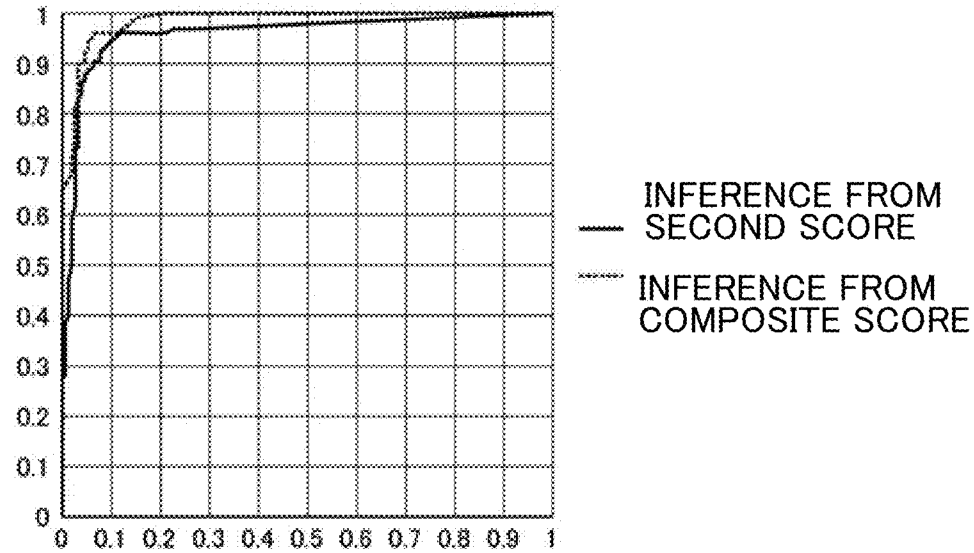
FIG. 18 is a drawing illustrating effects of Example 1.

Referring to FIG. 18, it can be understood that inferring disorders or symptoms by using the composite scores has better inference accuracy than cases in which disorders or symptoms are inferred by calculating the second scores using the learned ResNet and by utilizing these second scores.

Example 2

Example 2 is described next. In Example 1, it was inferred whether or not the subject is "CI", but Example 2 infers to which of "CI", "MDs", and "CTRL" the subject corresponds.

FIG. 19 is results in a case in which the second scores are calculated by using the learned ResNet, and disorders or symptoms are inferred by using only these second scores. FIG. 20 is results in a case in which, in the same way as in the first embodiment, composite scores in which the first scores and the second scores are added together are calculated, and disorders or symptoms are inferred by using these composite scores.

FIG. 21 is results in a case in which, in the same way as in the second embodiment, composite scores, in which the second scores that are calculated by using a known neural network and the first scores are added together, are calculated, and disorders or symptoms are inferred by using these composite scores. Note that the results of FIG. 21 are results in a case of using a neural network in which there is one hidden layer, at the time of calculating the second scores.

FIG. 22 is results in a case in which, in the same way as in the second embodiment, composite scores, in which the second scores that are calculated by using a known neural network and the first scores are added together, are calculated, and disorders or symptoms are inferred by using these composite scores. Note that the results of FIG. 22 are results in a case of using a neural network in which there are two hidden layers, at the time of calculating the second scores.

Referring to FIG. 19 through FIG. 22, it can be understood that the inferring accuracy is higher when inferring disorders or symptoms by using the composite scores, than when inferring disorders or symptoms by using only the second scores. Moreover, it can be understood that, at the time of calculating the first scores, the inferring accuracy is better when a neural network is used.

From the above results, it can be understood that, in accordance with the information processing systems of the first through fourth embodiments, it can be more accurately inferred whether or not a user has a psychological disorder, a neurological disorder or a symptom of these, than in a case in which a psychological disorder, a neurological disorder or a symptom of these is inferred by using parameters extracted from time series data of a voice.

Note that the technique of the present disclosure is not limited to the above-described embodiments, and various modifications and applications are possible within a scope that does not depart from the gist of this invention.

For example, although the present specification describes embodiments in which the program is installed in advance, the program can be also provided by being stored on a computer-readable recording medium.

Note that any of various types of processors other than a CPU may execute the processing that is executed due to the CPU reading-out software (the program) in the above embodiments. Examples of processors in this case include PLDs (Programmable Logic Devices) whose circuit structure can be changed after production such as FPGAs (Field-Programmable Gate Arrays) and the like, and dedicated electrical circuits that are processors having circuit structures that are designed for the sole purpose of executing specific processings such as ASICs (Application Specific Integrated Circuits) and the like, and the like. Further, a GPGPU (General-purpose graphics processing unit) may be used as the processor. Further, the respective processings may be executed by one of these various types of processors, or may be executed by a combination of two or more of the same type or different types of processors (e.g., plural FPGAs, or a combination of a CPU and an FPGA, or the like). Further, the hardware structures of these various types of processors are, more specifically, electrical circuits that combine circuit elements such as semiconductor elements and the like.

The above respective embodiments describe forms in which the program is stored in advance (is installed) in the storage, but the present disclosure is not limited to this. The program may be provided in a form of being stored on a non-transitory storage medium such as a CD-ROM (Compact Disk Read Only Memory), a DVD-ROM (Digital Versatile Disk Read Only Memory), a USB (Universal Serial Bus) memory, or the like. Further, the program may be in a form of being downloaded from an external device over a network.

Further, the respective processings of the present embodiments may be structured by a computer or a server or the like having a general-purpose computing processing device and storage device and the like, and the respective processings may be executed by a program. This program is stored in the storage device, but can also be recorded on a recording medium such as a magnetic disk, an optical disk, a semiconductor memory or the like, and can also be provided over a network. Of course, all of the other structural elements also do not have to be realized by a single computer or server, and may be realized by being divided among plural computers connected by a network.

Further, although the above embodiments describe examples of cases in which the sum of the first score and the second score is used as the composite score, the present disclosure is not limited to this. For example, a weighted sum of the first score and the second score may be used as the composite score.

Further, although the above embodiments describe examples of cases in which the calculation model is expressed by the above linear equations or neural network, the present disclosure is not limited to this. The calculation model may be another model, and, for example, nonlinear coupling such as logistic regression may be used. Further, the learned model may be a model other than ResNet.

Further, the first score in the above embodiments may include any one of a first psychological disorder or symptom score expressing the extent to which the user has a psychological disorder or symptom, a first neurological disorder or symptom score expressing the extent to which the user has a neurological disorder or symptom, and a first healthy score expressing the extent to which the user does not have any psychological disorder or symptom and neurological disorder or symptom. In this case, the second score includes any one of a second psychological disorder or symptom score expressing the extent to which the user has a psychological disorder or symptom, a second neurological disorder or symptom score expressing the extent to which the user has a neurological disorder or symptom, and a second healthy score expressing the extent to which the user does not have any psychological disorder or symptom and neurological disorder or symptom. Further, at the time of calculating the composite score, the composite score is calculated by combining the first psychological disorder or symptom score and the second psychological disorder or symptom score, combining the second psychological disorder or symptom score and the first neurological disorder or symptom score, combining the first healthy score and the second healthy score.

Further, although the above embodiments describe examples of cases in which a spectrogram image is generated as the image corresponding to the voice data, the present disclosure is not limited to this. Any image may be used provided that it is an image that corresponds to voice data. For example, the waveform itself of the voice data D illustrated in above-described FIG. 4 may be made into an image, and that image may be inputted to a learned model, and the second score may be calculated. In this case, for example, the information processing system inputs a feature amount extracted from the voice data into a first learned model that has been learned in advance and is for calculating, from the feature amount, a score expressing the extent of a psychological disorder, a neurological disorder or a symptom of these, and calculates a first score expressing the extent to which the user has a psychological disorder, a neurological disorder or a symptom of these. Further, the information processing system inputs the image generated from the voice data into a second learned model that has been learned in advance and is for calculating, from the image, a score expressing the extent of a psychological disorder, a neurological disorder or a symptom of these, and calculates a second score expressing the extent to which the user has a psychological disorder, a neurological disorder or a symptom of these.

All publications, patent applications, and technical standards mentioned in the present specification are incorporated by reference into the present specification to the same extent as if such individual publication, patent application, or technical standard was specifically and individually indicated to be incorporated by reference.

The invention claimed is:

1. An information processing apparatus comprising:

at least one memory, and at least one processor coupled to the memory, wherein the processor is configured to:

acquire voice data that is time series data of a voice uttered by a user;

conduct a frequency analysis on the voice data, wherein the frequency analysis includes determining an intensity of a frequency component;

generate a spectrogram image of the voice data, wherein the spectrogram image includes a pixel value corresponding to the intensity of the frequency component;

extract a first feature amount, which is a predetermined acoustic parameter, from the voice data to input the spectrogram image generated to a learned neural network model, and extract a second feature amount, which comprises values output from an intermediate layer of the learned neural network model;

calculate a score, which expresses an extent to which the user has a psychological disorder or a neurological disorder, or a psychological disturbance symptom or a cognitive impairment symptom, on the basis of the first feature amount and the second feature amount and a calculation model that is set in advance and is for calculating, from the first feature amount and the second feature amount, a score expressing an extent of a psychological disorder or a neurological disorder, or a psychological disturbance symptom or a cognitive impairment symptom; and infer whether or not the user has any disorder or symptom, in accordance with the score, wherein the learned neural network model is a learned neural network model that has been learned in advance by teacher data in which a spectrogram image for learning, and a correct answer label expressing a disorder or symptom of a user who uttered the voice data corresponding to the spectrogram image for learning, are associated with one another.

2. The information processing apparatus of claim 1, wherein:

the calculation model that is set in advance is a first learned model that has been learned in advance and is for calculating, from the feature amount, a score expressing an extent of a psychological disorder or a neurological disorder, or a psychological disturbance symptom or a cognitive impairment symptom, the learned model, which has been learned in advance and is for calculating, from the spectrogram image, a score expressing the extent of a psychological disorder or a neurological disorder, or a psychological disturbance symptom or a cognitive impairment symptom, is a second learned model, wherein the processor is configured to:

input the feature amount into the first learned model, and calculates the first score, and input the spectrogram image into the second learned model, and calculates the second score.

3. The information processing apparatus of claim 1, wherein the processor is configured to calculate an extent to which the user has a psychological disorder or a neurological disorder, or a psychological disturbance symptom or a cognitive impairment symptom, in accordance with a sum of the first score and the second score.

4. The information processing apparatus of claim 1, wherein the processor is configured to calculate an extent to which the user has a psychological disorder or a neurological disorder, or a psychological disturbance symptom or a cognitive impairment symptom, in accordance with a weighted sum of the first score and the second score.

5. The information processing apparatus of claim 1, wherein:

the first score includes any one of a first psychological disorder or symptom score expressing an extent to which the user has a psychological disorder or symptom, a first neurological disorder or symptom score expressing an extent to which the user has a neurological disorder or symptom, or a first healthy score expressing an extent to which the user does not have any psychological disorder or symptom or neurological disorder or symptom, the second score includes any one of a second psychological disorder or symptom score expressing an extent to which the user has a psychological disorder or symptom, a second neurological disorder or symptom score expressing an extent to which the user has a neurological disorder or symptom, or a second healthy score expressing an extent to which the user does not have any psychological disorder or symptom or neurological disorder or symptom, and the composite score is calculated by:

combining the first psychological disorder or symptom score and the second psychological disorder or symptom score, combining the second psychological disorder or symptom score and the first neurological disorder or symptom score, or combining the first healthy score and the second healthy score.

6. An information processing system, comprising a user terminal having a microphone, and the information processing apparatus of claim 1, wherein:

the user terminal transmits the voice data, which is acquired by the microphone, to the information processing apparatus, the processor of the information processing apparatus being configured to:

acquire the voice data transmitted from the user terminal, transmit, to the user terminal, results of inference, and the user terminal receives the results of inference transmitted from the information processing apparatus.

7. An information processing program executable by a computer to perform processing, comprising:

at least one memory and at least one processor coupled to the memory, wherein the processor is configured to:

acquire voice data that is time series data of a voice uttered by a user;

conduct a frequency analysis on the voice data, wherein the frequency analysis includes determining an intensity of a frequency component;

generate a spectrogram image of the voice data, wherein the spectrogram image includes a pixel value corresponding to the intensity of the frequency component;

extract a feature amount, which is a predetermined acoustic parameter, from the voice data, to input the generated spectrogram image to a learned neural network and extract a second feature amount which comprises values output from an intermediate layer of the learned neural network model;

calculate a score, which expresses an extent to which the user has a psychological disorder or a neurological disorder, or a psychological disturbance symptom or a cognitive impairment symptom, on the basis of the first feature amount and the second feature amount and a calculation model that is set in advance and is for calculating, from the first feature amount, a score expressing an extent of a psychological disorder or a neurological disorder, or a psychological disturbance symptom or a cognitive impairment symptom; and infer whether or not the user has any disorder or symptom, in accordance with the score, wherein the learned model is a learned model that has been learned in advance by teacher data in which a spectrogram image for learning, and a correct answer label expressing a disorder or symptom of a user who uttered the voice data corresponding to the spectrogram image for learning, are associated with one another.

8. An information processing apparatus, comprising:

at least one memory and at least one processor coupled to the memory, wherein the processor is configured to:

acquire voice data that is time series data of a voice uttered by a user;

conduct a frequency analysis on the voice data, wherein the frequency analysis includes determining an intensity of a frequency component;

generate an image corresponding to the voice data wherein the image includes a pixel value corresponding to the intensity of the frequency component extract a first feature amount, which is a predetermined acoustic parameter, from the voice data;

input the first feature amount into a first learned model that has been learned in advance and is for calculating, from the feature amount, a score expressing an extent of a psychological disorder or a neurological disorder, or a psychological disturbance symptom or a cognitive impairment symptom, and to calculate a first score expressing an extent to which the user has a psychological disorder or a neurological disorder, or a psychological disturbance symptom or a cognitive impairment symptom; and infer whether or not the user has any disorder or symptom, in accordance with the score, wherein the learned neural network model is a learned neural network model that has been learned in advance by teacher data in which a spectrogram image for learning, and a correct answer label expressing a disorder or symptom of a user who uttered the voice data corresponding to the spectrogram image for learning, are associated with one another.

9. An information processing method comprising:

by a processor:

acquiring voice data that is time series data of a voice uttered by a user;

conducting a frequency analysis on the voice data, wherein the frequency analysis includes determining an intensity of a frequency component;

generating a spectrogram image of the voice data, wherein the spectrogram image includes a pixel value corresponding to the intensity of the frequency component;

extracting a feature amount, which is a predetermined acoustic parameter, from the voice data, to input the generated spectrogram image to a learned neural network model, and extracting a second feature amount, which comprises values output from an intermediate layer of the learned neural network model;

calculating a first score, which expresses an extent to which the user has a psychological disorder or a neurological disorder, or a psychological disturbance symptom or a cognitive impairment symptom, on the basis of the first feature amount and the second feature amount and a calculation model that is set in advance and is for calculating, from the first feature amount and the second feature amount, a score expressing an extent of a psychological disorder or a neurological disorder, or a psychological disturbance symptom or a cognitive impairment symptom; and inferring whether or not the user has any disorder or symptom, in accordance with the composite score, wherein the learned neural network model is a learned neural network model that has been learned in advance by teacher data in which a spectrogram image for learning, and a correct answer label expressing a disorder or symptom of a user who uttered the voice data corresponding to the spectrogram image for learning, are associated with one another.

10. A non-transitory storage medium storing an information processing program executable by a computer to perform processing, the processing comprising:

acquiring voice data that is time series data of a voice uttered by a user;

conducting a frequency analysis on the voice data, wherein the frequency analysis includes determining an intensity of a frequency component generating a spectrogram image of the voice data, wherein the spectrogram image includes a pixel value corresponding to the intensity of the frequency component;

extracting a feature amount, which is a predetermined acoustic parameter, from the voice data, to input the generated spectrogram image to a learned neural network model, and extracting a second feature amount, which comprises values output from an intermediate layer of the learned neural network model;

calculating a first score, which expresses an extent to which the user has a psychological disorder or a neurological disorder, or a psychological disturbance symptom or a cognitive impairment symptom, on the basis of the first feature amount and the second feature amount and a calculation model that is set in advance and is for calculating, from the first feature amount and second feature amount, a score expressing an extent of a psychological disorder or a neurological disorder, or a psychological disturbance symptom or a cognitive impairment symptom; and inferring whether or not the user has any disorder or symptom, in accordance with the composite score, wherein the learned neural network model is a learned neural network model that has been learned in advance by teacher data in which a spectrogram image for learning, and a correct answer label expressing a disorder or symptom of a user who uttered the voice data corresponding to the spectrogram image for learning, are associated with one another.

* * * * *